(12) United States Patent
Chung et al.

(10) Patent No.: US 9,233,957 B2
(45) Date of Patent: Jan. 12, 2016

(54) 5-CARBAMOYL-ADAMANTAN-2-YL AMIDE DERIVATIVES, PHARMACEUTICALLY ACCEPTABLE SALTS THEREOF AND PREPARATION PROCESS THEREOF

(75) Inventors: Coo-Min Chung, Daejeon (KR); Choon-Ho Ryu, Daejeon (KR); Yoon-Kyeong Lee, Seoul (KR); Jin-Sook Moon, Gyeongsangnam-do (KR); Hye-Sung Lee, Daejeon (KR); Seon-Jeong Lee, Daejeon (KR); Kyung-Seok Oh, Daejeon (KR)

(73) Assignee: SK BIOPHARMACEUTICALS CO., LTD., Seoul (KR)

( * ) Notice: Subject to any disclaimer, the term of this patent is extended or adjusted under 35 U.S.C. 154(b) by 279 days.

(21) Appl. No.: 14/123,043

(22) PCT Filed: Jun. 11, 2012

(86) PCT No.: PCT/KR2012/004602
§ 371 (c)(1),
(2), (4) Date: Nov. 27, 2013

(87) PCT Pub. No.: WO2012/169863
PCT Pub. Date: Dec. 13, 2012

(65) Prior Publication Data
US 2014/0128427 A1    May 8, 2014

(30) Foreign Application Priority Data

Jun. 10, 2011 (KR) .................... 10-2011-0056060
Jun. 11, 2012 (KR) .................... 10-2012-0062049

(51) Int. Cl.
| | | |
|---|---|---|
| C07D 207/34 | (2006.01) | |
| C07D 213/81 | (2006.01) | |
| C07D 213/89 | (2006.01) | |
| C07D 215/48 | (2006.01) | |
| C07D 215/60 | (2006.01) | |
| C07D 417/04 | (2006.01) | |
| C07D 333/38 | (2006.01) | |
| C07D 261/10 | (2006.01) | |
| C07D 307/56 | (2006.01) | |
| C07D 261/18 | (2006.01) | |
| C07D 307/68 | (2006.01) | |
| C07D 401/04 | (2006.01) | |
| C07D 413/04 | (2006.01) | |
| C07D 413/12 | (2006.01) | |

(52) U.S. Cl.
CPC ............ *C07D 417/04* (2013.01); *C07D 207/34* (2013.01); *C07D 213/81* (2013.01); *C07D 213/89* (2013.01); *C07D 215/48* (2013.01); *C07D 215/60* (2013.01); *C07D 261/10* (2013.01); *C07D 261/18* (2013.01); *C07D 307/56* (2013.01); *C07D 307/68* (2013.01); *C07D 333/38* (2013.01); *C07D 401/04* (2013.01); *C07D 413/04* (2013.01); *C07D 413/12* (2013.01)

(58) Field of Classification Search
CPC .. C07D 207/34; C07D 213/81; C07D 213/89; C07D 215/48; C07D 215/60; C07D 261/10; C07D 261/18; C07D 307/56; C07D 307/68; C07D 333/38; C07D 401/04; C07D 413/04; C07D 413/12; C07D 417/04
See application file for complete search history.

(56) References Cited

U.S. PATENT DOCUMENTS

| | | | |
|---|---|---|---|
| 8,383,622 B2 | 2/2013 | Masuda et al. | ............. 514/236.5 |
| 2012/0225876 A1 | 9/2012 | Horiuchi et al. | ........... 514/235.2 |

FOREIGN PATENT DOCUMENTS

| | | | |
|---|---|---|---|
| CN | 101754954 | 6/2010 | ........... C07D 231/14 |
| EP | 2 163 543 | 3/2010 | ........... C07D 231/14 |
| WO | WO 2011/049520 | 4/2011 | ........... C07D 405/12 |
| WO | WO 2011/059021 | 5/2011 | ........... C07D 451/02 |
| WO | WO 2011/068927 | 6/2011 | ............. A61K 31/56 |

OTHER PUBLICATIONS

Extended European Search Report, dated Sep. 2, 2014, in EP 12797254.5.
Andrews, et al. (2003) "Effects of the 11β-hydroxysteroid dehydrogenase inhibitor carbenoxolone on insulin sensitivity in men with type 2 diabetes." *J. Clin. Endocrinol. Metab.*, 88(1):285-291.
Hermanowaski-Vosatka, et al. (2005) "11β-HSD1 inhibition ameliorates metabolic syndrome and prevents progression of atherosclerosis in mice." *JEM*, 202(4):514-527.

(Continued)

*Primary Examiner* — Valerie Rodriguez-Garcia
(74) *Attorney, Agent, or Firm* — Harness, Dickey & Pierce, P.L.C.

(57) ABSTRACT

Provided are a novel derivative of 5-carbamoyl adamantan-2-yl amide of Formula (I),

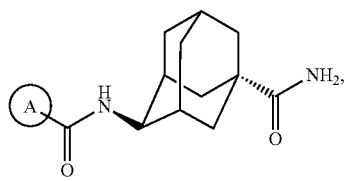

Formula (I)

or a pharmaceutically acceptable salt thereof, and a pharmaceutical use thereof for inhibiting the activity of 11β-hydroxystreroid dehydrogenase type 1 (11b-HSD1) or for preventing and/or treating various diseases mediated by 11β-hydroxystreroid dehydrogenase type 1.

20 Claims, No Drawings

(56) References Cited

OTHER PUBLICATIONS

Kotelevtsev, et al. (1997) "11β-hydroxysteroid dehydrogenase type 1 knockout mice show attenuated glucocorticoid-inducible responses and resist hyperglycemia on obesity or stress." *Proc. Natl. Acad. Sci. USA*, 94:14924-14929.

Kwon, et al. (2008) "Crif1 is a novel transcriptional coactivator of STAT3." *The EMBO Journal*, 27:642-653.

Masuzaki, et al. (2001) "A transgenic model of visceral obesity and the metabolic syndrome." *Science*, 294:2166.

Masuzaki, et al. (2003) "Transgenic amplification of glucocorticoid action in adipose tissue causes high blood pressure in mice." *J. Clin. Invest.*, 112(1):83.

Morton, et al. (2001) "Lipids and Lipoproteins: Improved lipid and lipoprotein profile, hepatic insulin sensitivity, and glucose tolerance in 11β-hydroxysteroid dehydrogenase type 1 null mice." *J. Biol. Chem.*, 276:41293-41300.

Rauz, et al. (2003) "Inhibition of 11β-hydroxysteroid dehydrogenase type 1 lowers intraocular pressure in patients with ocular hypertension." *Q. J. Med.*, 96:481-490.

Roche, et al. (2009) "Discovery and structure-activity relationships of pentanedioic acid diamides as potent inhibitors of 11β-hydroxysteroid dehydrogenase type 1." *Bioorganic & Medicinal Chemistry Letters*, 19:2674-2678.

Vicker, et al. (2007) "Novel non-steroidal inhibitors of human 11β-hydroxysteroid dehydrogenase type 1*." *The Journal of Steroid Biochemistry and Molecular Biology*, 104(3):123-129.

Walker, et al. (1995) "Carbenoxolone increases hepatic insulin sensitivity in man: a novel role fr 11-oxosteroid reductase in enhancing glucocorticoid receptor activation." *J. Clin. Endocrinol. Metab.*, 80(11):3155-3159.

International Search Report (ISR) and Written Opinion in PCT/KR2012/004602, dated Jan. 3, 2013.

5-CARBAMOYL-ADAMANTAN-2-YL AMIDE DERIVATIVES, PHARMACEUTICALLY ACCEPTABLE SALTS THEREOF AND PREPARATION PROCESS THEREOF

CROSS-REFERENCE TO RELATED APPLICATIONS

This application is a national phase application of PCT Application No. PCT/KR2012/004602, filed on June, 2012, which claims the benefit and priority to Korean Patent Application No. 10-2012-0062049, filed Jun. 11, 2012 and to Korean Patent Application No. 10-2011-0056060, filed Jun. 10, 2011. The entire disclosures of the applications identified in this paragraph are incorporated herein by references.

BACKGROUND OF THE INVENTION (a) Field of the Invention

The present invention relates to derivatives of 5-carbamoyl-adamantan-2-yl amide, pharmaceutically acceptable salts thereof, and uses of the 5-carbamoyl-adamantan-2-yl amide derivatives and/or pharmaceutically acceptable salts thereof for inhibiting the activity of 11β-hydroxysteroid dehydrogenase type 1 (11b-HSD1) and/or for preventing and/or treating of various diseases mediated by 11β-hydroxysteroid dehydrogenase type 1.

(b) Description of the Related Art

Glucocorticoid (cortisol in humans, corticosterone in mice and rats), a type of adrenocorticosteroid, plays critical roles of regulating a range of metabolism and homeostasis, getting involved in a stress-related reaction, and the like. Such actions of glucocorticoid are performed via bonding the active glucocorticoid with a glucocorticoid receptor (GR). Interconversion between the active 11-hydroxy glucocorticoid (cortisol in humans) and the inactive 11-keto glucocorticoid (cortisone in humans) is catalyzed by the endoenzyme, 11β-hydroxysteroid dehydrogenase (11b-HSD), which is present in two isoforms. 11β-hydroxysteroid dehydrogenase type 1 (11b-HSD1) takes a part in turning an inactive 11-keto metabolite into an active 11-hydroxy metabolite, while 11β-hydroxysteroid dehydrogenase type 2 plays a role of switching the active form to the inactive form. The active 11-hydroxy glucocorticoid engages in regulating phosphoenolpyruvate carboxykinase (PEPCK), which is a major enzyme for gluconeogenesis through the bonding with the intracellular glucocorticoid receptor.

Gluconeogenesis is a process of glucose synthesis process that takes place in the liver, and it involves the actions of major enzymes such as phosphoenolpyruvate carboxykinase (PEPCK) promoting the conversion of oxaloacetate into phosphoenolpyruvate and glucose-6-phosphatase (G6Pase) facilitating hydrolysis of glucose-6-phophate to provide free glucose. In this regard, the rate-controlling step determining the rate of gluconeogenesis is the conversion of oxaloacetate into phosphoenolpyruvate, which is promoted by the phosphoenolpyruvate carboxykinase.

In particular, fasting brings about up-regulation of both phosphoenolpyruvate carboxykinase and glucose-6-phosphatase, resulting in an increased rate of gluconeogenesis and thereby the blood glucose level is also getting higher. Accordingly, inhibiting the activity of 11β-hydroxysteroid dehydrogenase type 1 (11b-HSD1) may regulate the concentration of the active 11-hydroxy glucocorticoid, control phosphoenolpyruvate carboxykinase, and decrease the blood glucose level, and thereby it can be a useful approach for treating diabetes.

Besides the foregoing biochemical reviews, some small-scale clinical researches for humans or transformed mice have evidenced the potential for treating diabetes via the inhibition of 11β-hydroxysteroid dehydrogenase type 1.

An experiment conducted with using transformed mice has revealed that modulating the activity of 11β-hydroxysteroid dehydrogenase type 1 may bring forth beneficial effects of treating diabetes and metabolic syndrome. For example, in case of knockout mice lacking a gene of 11β-hydroxysteroid dehydrogenase type 1, fasting led to no increase in the amount of phosphoenolpyruvate carboxykinase and glucose-6-phophatase and they did not develop hyperglycemia associated with stress or obesity, as well (See, Kotolevtsev Y. et al., *Proc. Natl. Acad. Sci. USA* 1997, 94, 14924). In addition, the knockout mice lacking a gene of 11β-hydroxysteroid dehydrogenase type 1 showed an improvement on a lipid profile and insulin sensitivity and was found to have a glucose tolerance function (See, Morton et al., *J. Biol. Chem.* 2001, 276, 41293). A research was further conducted regarding mice with the over-expressed gene of 11β-hydroxysteroid dehydrogenase type 1. The mouse with the over-expressed gene of 11β-hydroxysteroid dehydrogenase type 1 showed an increased concentration of corticosterone and an enhanced activity of 11β-hydroxysteroid dehydrogenase type 1 in adipose tissue. It also induces phenotypes of abdominal obesity and syndrome-X. In particular, when being fed on a high fat diet, the mouse showed a considerably increased level of obesity, and it also had a high level of blood glucose and insulin even when being fed on a low fat diet. Moreover, they exhibited impaired glucose tolerance and insulin resistance (See, Masuzaki et al., *Science* 2001, 294, 2166).

In addition, a small-scale clinical trial for carbenoxolone, a non-selective inhibitor of 11β-hydroxysteroid dehydrogenase type 1, confirmed that 11β-hydroxysteroid dehydrogenase type 1 may have an effect of treating diabetes. There was a research discovering that carbenoxolone increases systemic insulin sensitivity through a decrease in a liver glucose production (See, Walker Et al., *J. Clin. Endocrinol. Metab.* 1995, 80, 3155). In another research, diabetic patients being administered with carbenoxolone were found to have a decreased level of glucose production even when they were administered with glucagon, and they also showed a decreased level of glycogen decomposition. However, such phenomenon was not observed in a healthy person, though (See, Andrews et al. *J. Clin. Endocrinol. Metab.* 2003, 22, 285). Such results indicated that regulating the activity of 11β-hydroxysteroid dehydrogenase type 1 may have an effect of treating diabetes and metabolic syndrome.

Besides, recent research has showed that the inhibition of 11β-hydroxysteroid dehydrogenase type 1 enables amelioration of hypertension (See, Masuzaki et al., J. Clin. Invest. 2003, 12, 83; Rauz et al., QJM 2003, 96, 481).

With taking all these reports into account, one may draw a conclusion that the inhibition of 11β-hydroxysteroid dehydrogenase type 1 will be able to present safe and effective approaches for treating symptoms of various diseases such as diabetes, metabolic syndrome, and the like.

SUMMARY OF THE INVENTION

Thus, an embodiment of the present invention provides a 5-carbamoyl-adamantan-2-yl amide derivative or a pharmaceutically acceptable salt thereof.

Another embodiment provides a composition for inhibiting the activity of 11β-hydroxysteroid dehydrogenase type 1 (11b-HSD1) containing the 5-carbamoyl-adamantan-2-yl amide derivative and/or the pharmaceutically acceptable salt thereof as an active ingredient.

Another embodiment provides a composition for preventing and/or treating various diseases mediated by 11β-hydroxysteroid dehydrogenase type 1 containing the 5-carbamoyl-adamantan-2-yl amide derivative and/or the pharmaceutically acceptable salt thereof as an active ingredient.

Another embodiment provides a method of inhibiting the activity of 11β-hydroxysteroid dehydrogenase type 1 comprising the step of administering a therapeutically effective amount of the 5-carbamoyl-adamantan-2-yl amide derivative and/or the pharmaceutically acceptable salt thereof as an active ingredient to a patient in need thereof.

Another embodiment provides a method preventing and/or treating various diseases mediated by 11β-hydroxysteroid dehydrogenase type 1 comprising the step of administering a therapeutically effective amount of the 5-carbamoyl-adamantan-2-yl amide derivative and/or the pharmaceutically acceptable salt thereof as an active ingredient to a patient in need thereof.

Another embodiment provides the 5-carbamoyl-adamantan-2-yl amide derivative and/or the pharmaceutically acceptable salt thereof for the use in inhibiting the activity of 11β-hydroxysteroid dehydrogenase type 1 as an active ingredient.

Another embodiment provides the 5-carbamoyl-adamantan-2-yl amide derivative and/or the pharmaceutically acceptable salt thereof for the use in preventing and/or treating various diseases mediated by 11β-hydroxysteroid dehydrogenase type 1 as an active ingredient.

Another embodiment provides a use of the 5-carbamoyl-adamantan-2-yl amide derivative and/or the pharmaceutically acceptable salt thereof in preparing a medicament for inhibiting the activity of 11β-hydroxysteroid dehydrogenase type 1 (11b-HSD1) as an active ingredient.

Still another embodiment provides a use of the 5-carbamoyl-adamantan-2-yl amide derivative and/or the pharmaceutically acceptable salt thereof in preparing a medicament for preventing and/or treating various diseases mediated by 11β-hydroxysteroid dehydrogenase type 1 as an active ingredient.

DETAILED DESCRIPTION OF THE EMBODIMENT

The compounds, the compositions, the methods, and the uses of the present invention may be applied to mammals including humans, and have some benefits of effectively and selectively inhibiting 11β-hydroxysteroid dehydrogenase type 1, thereby being advantageously used for treating diseases caused by abnormal modulation of 11β-hydroxysteroid dehydrogenase type 1 such as diabetes, metabolic syndrome, and the like.

First, an embodiment provides a derivative of 5-carbamoyl-adamantan-2-yl amide represented by Chemical Formula I or a pharmaceutically acceptable salt thereof:

[Chemical Formula I]

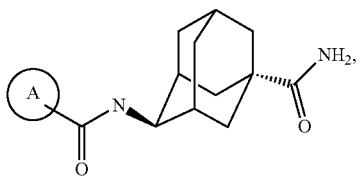

in the above formula, ring A may be an aryl group or a heteroaryl group selected from the group consisting of Chemical Formulae (II) to (VIII):

(II)

(III)
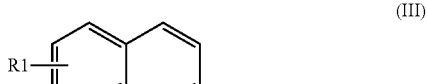

(IV)
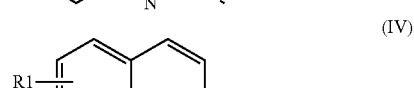

(V)

(VI)

(VII)
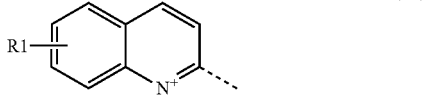

(VIII)

in which X may be O, S, or N—Y,

Y may be selected from the group consisting of H, a linear or branched alkyl group of C1 to C5, and a cyclic alkyl group of C3 to C5, R1, which is linked to any one of the aromatic carbons of ring A, may be selected from the group consisting of H; a linear or branched alkyl group of C1 to C5; a cyclic alkyl group of C3 to C5; O—R3; —N(R4)R5; and a phenyl, a pyridine, a furan, a thiazol, a thiophene, a hydro-1H-isoquinoline, and an isoxazole groups, one to three hydrogen atoms of which is (are) substituted with R2, R2 may be selected from the group consisting of H, a halogen atom (e.g., F, Cl, or Br), a linear or branched alkyl group of C1 to C5, a cyclic alkyl group of C3 to C5, a trifluoromethyl group, a nitro group, —O—R6, and —N(R7)R8;

R3 may be selected from the group consisting of H, a linear or branched alkyl group of C1 to C4, a cyclic alkyl group of C3 to C5, —CH$_2$-cyclic alkyl of C5 to C6, —CH$_2$-aryl of C6 to C10, and —CH$_2$-heteroaryl of C2 to C8 comprising at least one selected from the group consisting of O, N, and S on the aromatic ring;

R4 and R5, which are the same with or different from each other, may be independently selected from the group consisting of H and a linear or branched alkyl group of C1 to C5, or R4 and R5 may be linked to form a 5-7 membered ring, wherein the 5-7 membered ring formed by linkage of R4 and R5 may a non-substituted one or have a phenyl group as a substituent;

R6 may be selected from the group consisting of H and a linear or branched alkyl group of C1 to C3; and R7 and R8, which are the same with or different from each other, may be independently selected from the group consisting of H and a linear or branched alkyl group of C1 to C3, or R7 and R8 may be linked to form a 5-7 membered ring.

In an embodiment, ring A may be a heteroaryl group of Chemical Formula (II):

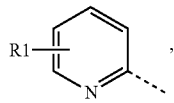

(II)

wherein R1, which is linked to any one of aromatic carbons of ring A, may be selected from the group consisting of H; a linear or branched alkyl group of C1 to C5 (e.g., a methyl group); —O—R3 (in which R3 is a linear or branched alkyl group of C1 to C4 to form, for example, a methoxy, propoxy group, and the like; —CH₂-aryl of C6 to C10 to form, for example, a benzyl oxy group; or —CH₂-heteroaryl of C2 to C8 having at least one of O, N, and S on the aromatic ring to form, for example, a dimethyl oxazolyl methoxy group); N(R4)R5 [in which R4 and R5 are each independently selected from the group consisting of hydrogen and a linear or branched alkyl group of C1 to C5 (e.g., dimethylamino group, a propylamino group, a diethylamino group, and the like); R4 and R5 may be linked to form a 5-7 membered ring (e.g., a piperidine group); or the 5-7 membered ring may comprise a phenyl group as a substituent (e.g., a phenyl piperidine group)]; and 3,4-dihydro-1H-isoquinoline.

In other embodiments, ring A may be a heteroaryl group of Chemical Formula (III):

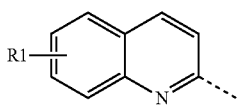

(III)

wherein R1, which is linked to any one of aromatic carbons of ring A, may be H, or O—R3 [in which R3 may be a linear or branched alkyl group of C1 to C4 (e.g., to form a methoxy group, an ethoxy group, a propoxy group, 1-methylethoxy group, 2-methylpropoxy group, 1-methylpropoxy group, and the like) or —CH₂-aryl of C6 to C10 (e.g., to form a benzyloxy group), or —CH₂-cyclic alkyl of C5 to C6].

In another embodiment, ring A is a heteroaryl group of Chemical Formula (IV):

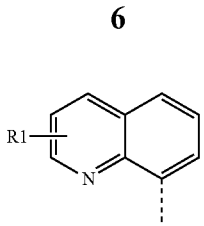

(IV)

wherein R1, which is linked to any one of aromatic carbons of ring A, may be H or a linear or branched alkyl group of C1 to C5.

In another embodiment, ring A is a heteroaryl group of Chemical Formula (V):

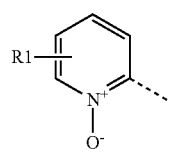

(V)

wherein R1, which is linked to any one of aromatic carbons of ring A, may be H, a linear or branched alkyl group of C1 to C5 (e.g., a methyl group), or —N(R4)R5 [in which R4 and R5 may be the same with or different from each other and are each independently selected from the group consisting of H and a linear or branched alkyl group of C1 to C5 (e.g., a dimethylamino group)].

In other embodiment, ring A is a heteroaryl group of Chemical Formula (VI):

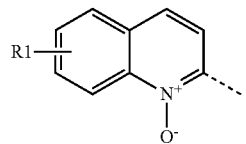

(VI)

wherein R1, which is linked to any one of aromatic carbons of ring A, may be H or a linear or branched alkyl group of C1 to C5.

In other embodiment, ring A is a heteroaryl group of Chemical Formula (VII):

(VII)

wherein X is O, S, or N—Y;

Y is a linear or branched alkyl group of C1 to C5;

R1, which is linked to any one of aromatic carbons of ring A, may be H, a linear or branched alkyl group of C1 to C5 (e.g., a methyl group), a phenyl group with one to three hydrogen atoms being substituted with R2 [in which R2 may be H, a halogen atom (e.g., a chlorophenyl group, a fluorophenyl group, a dichlorophenyl group, a difluorophenyl group, a trifluorophenyl group, and the like), a linear or branched alkyl group of C1 to C5 (e.g., a methylphenyl group), a nitro group (e.g., a nitrophenyl group), or an alkoxy group of C1 to C3 (e.g., a methoxy phenyl group)], or a thiophene group.

In another embodiment of the present invention, ring A is a heteroaryl group of Chemical Formula (VIII):

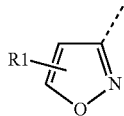 (VIII)

wherein R1, which is linked to any one of aromatic carbons of ring A, may be H, a linear or branched alkyl group of C1 to C5 (e.g., a t-butyl group), a phenyl with one to three hydrogen atoms substituted with R2, a furan, or a thiophene group, a thiazole group with one to three hydrogen atoms substituted with R2, or a hydroxyl group. R2 may be H, a halogen atom, a linear or branched alkyl group of C1 to C5, or a linear or branched alkoxy group of C1 to C3, where for example, in case of a phenyl group with one to three hydrogen atoms substituted with R2, R2 may be H, a halogen atom (e.g., a chlorophenyl or a fluorophenyl), a linear or branched alkyl group of C1 to C5 (e.g., a methyl phenyl group), or an alkoxy group of C1 to C3 (e.g., a methoxy phenyl group), and in case of a thiazole group with one to three hydrogen atoms being substituted with R2, R2 may be a linear or branched alkyl group of C1 to C5 (e.g., a methyl thiazole group).

In the present invention, specific examples of the compound being defined as Chemical Formula I include at least one selected from the group consisting of the following compounds:

N-(5-carbamoyl-2-adamantyl)-5-phenylfuran-2-carboxamide,
N-(5-carbamoyl-2-adamantyl)-5-(4-chlorophenyl)furan-2-carboxamide,
N-(5-carbamoyl-2-adamantyl)-5-(4-nitrophenyl)furan-2-carboxamide,
N-(5-carbamoyl-2-adamantyl)-5-(4-methylphenyl)furan-2-carboxamide,
5-t-butyl-N-(5-carbamoyl-2-adamantyl)-1,2-oxazole-3-carboxamide,
N-(5-carbamoyl-2-adamantyl)-5-(3-methylphenyl)-1,2-oxazole-3-carboxamide,
N-(5-carbamoyl-2-adamantyl)-5-(2-methoxyphenyl)-1,2-oxazole-3-carboxamide,
N-(5-carbamoyl-2-adamantyl)-5-(2-methylphenyl)-1,2-oxazole-3-carboxamide,
N-(5-carbamoyl-2-adamantyl)-5-(3-methoxyphenyl)-1,2-oxazole-3-carboxamide,
N-(5-carbamoyl-2-adamantyl)-5-(furan-3-yl)-1,2-oxazole-3-carboxamide,
N-(5-carbamoyl-2-adamantyl)-5-(thiophen-3-yl)-1,2-oxazole-3-carboxamide,
N-(5-carbamoyl-2-adamantyl)-5-(3-fluorophenyl)-1,2-oxazole-3-carboxamide,
N-(5-carbamoyl-2-adamantyl)-5-(4-chlorophenyl)-1,2-oxazole-3-carboxamide,
N-(5-carbamoyl-2-adamantyl)-5-(2-methyl-1,3-thiazol-4-yl)-1,2-oxazole-3-carboxamide,
N-(5-carbamoyl-2-adamantyl)-6-methylpyridine-2-carboxamide,
N-(5-carbamoyl-2-adamantyl)pyridine-2-carboxamide,
N-(5-carbamoyl-2-adamantyl)-1-methylpyrrole-2-carboxamide,
N-(5-carbamoyl-2-adamantyl)quinoline-2-carboxamide,
N-(5-carbamoyl-2-adamantyl)quinoline-8-carboxamide,
N-(5-carbamoyl-2-adamantyl)-8-hydroxyquinoline-2-carboxamide,
N-(5-carbamoyl-2-adamantyl)-5-thiophen-2-yl-thiophene-2-carboxamide,
N-(5-carbamoyl-2-adamantyl)thiophene-2-carboxamide,
N-(5-carbamoyl-2-adamantyl)-4-methylthiophene-2-carboxamide,
N-(5-carbamoyl-2-adamantyl)-5-methylthiophene-2-carboxamide,
N-(5-carbamoyl-2-adamantyl)-5-(4-fluorophenyl)furan-2-carboxamide,
N-(5-carbamoyl-2-adamantyl)-5-(3-chlorophenyl)furan-2-carboxamide,
N-(5-carbamoyl-2-adamantyl)-5-(2-chlorophenyl)furan-2-carboxamide,
N-(5-carbamoyl-2-adamantyl)-5-(4-methoxyphenyl)furan-2-carboxamide,
N-(5-carbamoyl-2-adamantyl)-5-(3,4-difluorophenyl)furan-2-carboxamide,
N-(5-carbamoyl-2-adamantyl)-5-(2-fluorophenyl)furan-2-carboxamide,
N-(5-carbamoyl-2-adamantyl)-5-(3,4-dichlorophenyl)furan-2-carboxamide,
N-(5-carbamoyl-2-adamantyl)-5-(3,5-dichlorophenyl)furan-2-carboxamide,
N-(5-carbamoyl-2-adamantyl)-5-(3-chlorophenyl)-1-methylpyrrole-2-carboxamide,
N-(5-carbamoyl-2-adamantyl)-1-methyl-5-phenylpyrrole-2-carboxamide,
N-(5-carbamoyl-2-adamantyl)-5-(4-chlorophenyl)-1-methylpyrrole-2-carboxamide,
N-(5-carbamoyl-2-adamantyl)-5-(4-fluorophenyl)-1-methylpyrrole-2-carboxamide,
N-(5-carbamoyl-2-adamantyl)-1-methyl-5-[4-(trifluoromethyl)phenyl]pyrrole-2-carboxamide,
N-(5-carbamoyl-2-adamantyl)-5-(2-chlorophenyl)-1-methylpyrrole-2-carboxamide,
N-(5-carbamoyl-2-adamantyl)-5-(2-fluorophenyl)-1-methylpyrrole-2-carboxamide,
N-(5-carbamoyl-2-adamantyl)-5-phenylthiophene-2-carboxamide,
N-(5-carbamoyl-2-adamantyl)-5-(4-chlorophenyl)thiophene-2-carboxamide,
N-(5-carbamoyl-2-adamantyl)-5-(3-chlorophenyl)thiophene-2-carboxamide,
N-(5-carbamoyl-2-adamantyl)-5-(2-chlorophenyl)thiophene-2-carboxamide,
N-(5-carbamoyl-2-adamantyl)-5-(2-fluorophenyl)thiophene-2-carboxamide,
N-(5-carbamoyl-2-adamantyl)-6-methoxypyridine-2-carboxamide,
N-(5-carbamoyl-2-adamantyl)-6-propoxypyridine-2-carboxamide,
N-(5-carbamoyl-2-adamantyl)-6-phenylmethoxypyridine-2-carboxamide,
N-(5-carbamoyl-2-adamantyl)-6-[(3,5-dimethyl-1,2-oxazol-4-yl)methoxy]pyridine-2-carboxamide,
N-(5-carbamoyl-2-adamantyl)-8-propoxyquinoline-2-carboxamide,
N-(5-carbamoyl-2-adamantyl)-8-methoxyquinoline-2-carboxamide,
N-(5-carbamoyl-2-adamantyl)-8-ethoxyquinoline-2-carboxamide,
N-(5-carbamoyl-2-adamantyl)-8-propan-2-yloxyquinoline-2-carboxamide,
N-(5-carbamoyl-2-adamantyl)-8-benzylmethoxyquinoline-2-carboxamide, N-(5-carbamoyl-2-adamantyl)-8-(2-methylpropoxy)quino-line-2-carboxamide,
N-(5-carbamoyl-2-adamantyl)-8-(cyclohexylmethoxy) quinoline-2-carboxamide,
8-butan-2-yloxy-N-(5-carbamoyl-2-adamantyl)quinoline-2-carboxamide,
N-(5-carbamoyl-2-adamantyl)-6-(dimethylamino)pyridine-2-carboxamide,
N-(5-carbamoyl-2-adamantyl)-6-piperidin-1-ylpyridine-2-carboxamide,
N-(5-carbamoyl-2-adamantyl)-6-(diethylamino)pyridine-2-carboxamide,
N-(5-carbamoyl-2-adamantyl)-6-(propylamino)pyridine-2-carboxamide,
N-(5-carbamoyl-2-adamantyl)6-(3,4-dihydro-1H-isoquino-line-2-yl)pyridine-2-carboxamide,
N-(5-carbamoyl-2-adamantyl)6-(4-phenylpiperidin-1-yl) pyridine-2-carboxamide,
N-(5-carbamoyl-2-adamantyl)-6-methyl-1-oxidopyridin-1-ium-2-carboxamide,
N-(5-carbamoyl-2-adamantyl)-1-oxidoquinolin-1-ium-2-carboxamide, and
N-(5-carbamoyl-2-adamantyl)-6-(dimethylamino)-1-oxi-dopyridin-1-ium-2-carboxamide.

The present inventors have discovered that a compound represented by Chemical Formula I possesses an excellent effect of inhibiting 11β-hydroxysteroid dehydrogenase type 1 (11β-HSD1), and also maintains the effect of inhibiting 11β-HSD1 for an extended period of time (See, Test examples and Table 1 to Table 3).

Such medicinal effects of the compound represented by Chemical Formula I may be retained by its all possible isomeric forms such as a racemate, an enantiomer, and a diastereomer, and by a pharmaceutically acceptable salt thereof.

Therefore, in another aspect of the present invention is provided a pharmaceutical composition comprising a therapeutically effective amount of at least one selected from the group consisting of a compound represented by Chemical Formula I and a pharmaceutically acceptable salt thereof as an effective ingredient. The pharmaceutical composition may further comprise a pharmaceutically acceptable carrier.

In preparing a medicine taking advantage of the medicinal effects of the compound represented by Chemical Formula I, the compound of Chemical Formula I may be in the form of any possible isomers such as a racemate, an enantiomer, and a diastereomer or in the form of a pharmaceutically acceptable salt thereof.

In particular, the pharmaceutical composition comprising a therapeutically effective amount of at least one selected from the group consisting of a compound represented by Chemical Formula I and a pharmaceutically acceptable salt thereof may be a composition for inhibiting 11β-hydroxysteroid dehydrogenase type 1.

Alternatively, the pharmaceutical composition comprising a therapeutically effective amount of at least one selected from the group consisting of a compound represented by Chemical Formula I and a pharmaceutically acceptable salt thereof may be a composition for prevention and/or treatment of diseases mediated (caused) by 11β-hydroxysteroid dehydrogenase type 1. The disease mediated by 11β-hydroxysteroid dehydrogenase type 1 may be at least one disease selected from the group consisting of diabetes (e.g., insulin dependent diabetes, non-insulin dependent diabetes, and the like), arthritis, obesity, impaired glucose tolerance, metabolic syndrome, hypertension, hyperlipidemia, atherosclerosis, and the like, and it may include any other diseases known to be mediated by 11β-hydroxysteroid dehydrogenase type 1.

The pharmaceutically acceptable salt may include any of addition salts of an acid or a base and their stereochemical isomers. The salts may be any one capable of maintaining an activity of their parent compounds while not leading to any undesirable effect and their types are not particularly limited. They may include organic and inorganic salts, and examples of them comprise the salts of acetic acid, nitric acid, aspartic acid, sulfonic acid, sulfuric acid, maleic acid, glutamic acid, formic acid, succinic acid, phosphoric acid, phthalic acid, tannic acid, tartaric acid, hydrobromic acid, propionic acid, benzene sulfonic acid, benzoic acid, stearic acid, esylic acid, butyric acid, bicarbonic acid, bisulfuric acid, bitartaric acid, oxalic acid, butylic acid, calcium edetate, camsilyic acid, carbonic acid, chlorobenzoic acid, citric acid, edetic acid, toluene sulfonic acid, edisylic acid, esylinic acid, fumaric acid, gluceptic acid, pamoic acid, gluconic acid, glycollylarsanilic acid, methyl nitric acid, polygalacturonic acid, hexylresorcinoic acid, malonic acid, hydrabamic acid, hydrochloric acid, hydroiodic acid, hydroxynaphtholic acid, icetionic acid, lactobionic acid, mandelic acid, estorlinic acid, mucic acid, naphsilic acid, muconic acid, p-nitromethansulfonic acid, hexamic acid, pantothenic acid, monohydrogen phosphoric acid, dihydrogen phosphoric acid, salicylic acid, sulfamic acid, sulfanilic acid, methansulfonic acid, and teoclic acid. Further, the types of the alkaline salts include, for example, an ammonium salt, salts of an alkali and alkaline earth metal such as lithium, sodium, potassium, magnesium, and calcium, a salt having an organic base such as benzathine, N-methyl-D-glucamine, and hydrabamine salts, and for example, a salt having an amino acid such as arginine and lysine. In addition, such types of a salt can be transformed into a free acid or a free base by treating the corresponding salts with an appropriate acid or base. The term "addition salt" includes a solvate which can be formed by a compound of Chemical Formula I and a salt thereof. The solvate compound can be, for example, a hydrate or an alcoholate.

The pharmaceutical composition may be formulated into various types for oral or parenteral administration. By way of an example, it can be formulated into any dosage form for oral administration such as tablets, pills, soft or hard capsules, solutions, suspensions, emulsions, syrups, granules, and elixirs. Besides the effective ingredient, such a dosage form for oral administration may further include any pharmaceutically acceptable carriers depending on a typical construction of each formulation, for examples, diluents such as lactose, dextrose, sucrose, mannitol, sorbitol, cellulose and/or glycine or lubricants such as silica, talc, steric acid and its magnesium or calcium salt, and/or polyethylene glycol.

In case the formulation for oral administration is in a tablet form, it may also comprise binding agents such magnesium aluminum silicate, starch paste, gelatin, gum tragacanth, methyl cellulose, sodium carboxymethyl cellulose, and/or polyvinyl pyrrolidone, and if desired, it may also include disintegrating agents such as alginic acid or its sodium salt, agar, starch, or a boiling mixture, and/or an absorbing agent, a colorant, a flavoring agent, or a sweetening agent.

The pharmaceutical composition may be formulated into a form of parenteral administration. In this case, it may be administered by means of parenteral administration methods such as a hypodermic injection, an intravenous injection, an intramuscular injection or an intrathoracic injection. In order for the pharmaceutical composition of the present invention to be formulated into a dosage form for parenteral administration, the effective ingredient (i.e., a derivative of Chemical Formula I or a pharmaceutically acceptable salt thereof) is mixed with a stabilizer or a buffering agent in water to prepare as a solution or a suspension, which is then produced as a unit dosage form such as an ample or a vial.

In addition, the pharmaceutical composition may be sterilized or may further comprise an adjuvant such as a preservative, a stabilizing agent, a hydrating agent, an emulsifying agent, or a salt for controlling osmotic pressure and/or a buffering agent, and it may further include other therapeutically beneficial substances and may be formulated in accordance with conventional methods of mixing, granulation, or coating.

The pharmaceutical composition may comprise the effective ingredient, i.e., a derivative of Chemical Formula I, its racemate, or a pharmaceutically acceptable salt thereof in an effective amount of 0.1 to 500 mg/kg (body weight), preferably 0.5 to 100 mg/kg (body weight) in case of mammals including a human, and such pharmaceutical compositions may be divided into one or two doses per day and administered via an oral or parenteral route.

In another aspect, the present invention provides a method of inhibiting 11β-hydroxysteroid dehydrogenase type 1, comprising the step of administering a therapeutically effective amount of a derivative of Chemical Formula I, its racemate, or a pharmaceutically acceptable salt thereof to a patient in need of inhibition of 11β-hydroxysteroid dehydrogenase type 1. The inhibition method may further comprise a step of identifying the patient who is in need of the inhibition of the activity of 11β-hydroxysteroid dehydrogenase type 1 prior to the step of administration.

In another aspect, the present invention provides a method of treating or preventing a disease mediated by 11β-hydroxysteroid dehydrogenase type 1, comprising the step of administering a therapeutically effective amount of a derivative of Chemical Formula I, its racemate, or a pharmaceutically acceptable salt thereof to a patient in need of the prevention or the treatment of the disease mediated by 11β-hydroxysteroid dehydrogenase type 1. The method of treatment or prevention may further comprise a step of identifying the patient who is in need of the prevention or the treatment of the disease mediated by 11β-hydroxysteroid dehydrogenase type 1 prior to the step of administration.

The disease mediated (caused) by 11β-hydroxysteroid dehydrogenase type 1 may be, for example, at least one selected from the group consisting of insulin dependent diabetes, non-insulin dependent diabetes, arthritis, obesity, impaired glucose tolerance, metabolic syndrome, hypertension, hyperlipidemia, atherosclerosis, and the like, and it may include any other diseases known to be associated with the activity of 11β-hydroxysteroid dehydrogenase type 1.

The patient may be a mammal, preferably a human.

In addition, a person of ordinary skill in the art may easily select a specific administration method and a therapeutically effective amount of a derivative of Chemical Formula I, its racemate, or a pharmaceutically acceptable salt thereof with no particular limitations, taking the types of the mammals to be administered and the disease, and the specific types of the derivative of Chemical Formula I and its inhibition activity against 11β-hydroxysteroid dehydrogenase type 1 into account. By way of an example, the administration of the derivative of Chemical Formula I, its racemate or a pharmaceutically acceptable salt thereof may be made with an effective amount of 0.1 to 500 mg/kg (body weight), preferably 0.5 to 100 mg/kg (body weight) per day, once or twice a day via an oral or parenteral route.

The derivative of Chemical Formula I, its racemate, or a pharmaceutically acceptable salt thereof may have an effect of inhibiting 11β-HSD1 for an extended period of time and thereby one may decrease the number of administration per day.

In another embodiment provides a method of preparing the compound of Chemical Formula I. The preparation of the compound of Chemical Formula I may be conducted by using a known compound or a compound easily prepared therefrom in perspective of a person of ordinary skill in the art regarding a chemical synthesis. Accordingly, the following explanations as to the method of preparing the compound of Chemical Formula I are merely presenting exemplary methods and if necessary, the sequence of each step may be selectively altered and does not limit the scope of the invention.

In an embodiment, the preparation method may comprise the steps of:

subjecting 4-oxoadamantane-1-carboxylic acid to amidation to prepare 4-oxoadamantane-1-carboxylic acid amide;

subjecting 4-oxoadamantane-1-carboxylic acid amide to amidation to prepare 4-aminoadamantane-1-carboxylic acid amide; and treating 4-aminoadamantane-1-carboxylic acid amide with an acid to produce a salt and conducting a recrystallization of the salt to prepare a pure (E) type of 4-aminoadamantane-1-carboxylic acid amide (See, Reaction Scheme 1).

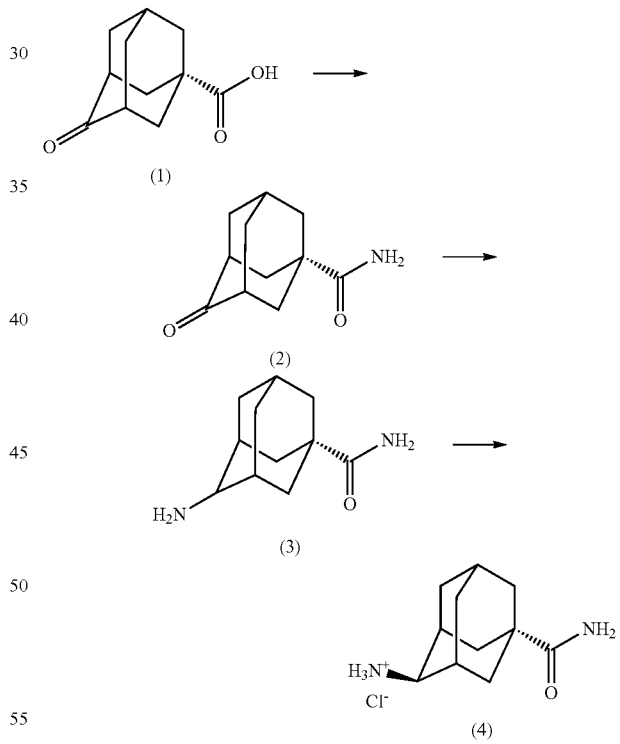

More detailed explanations on Reaction Formula 1 are as follows: 4-oxoadamantane-1-carboxylic acid (1) is treated with oxalic chloride and ammonia water to prepare 4-oxoadamantane-1-carboxylic acid amide (2), and the resulting compound is treated with ammonia and subjected to a reduction reaction by using hydrogen to produce 4-aminoadamantane-1-carboxylic acid amide (3). 4-aminoadamantane-1-carboxylic acid amide thus prepared is a mixture of (E) and (Z) types, which is made into a salt form by using hydrochloric acid and then subjected to recrystallization by using acetonitrile and water to yield a pure (E) type of 4-aminoadamantane-1-carboxylic acid amide (4).

In other embodiment, the production method may comprise a step of reacting a heteroaryl carboxylic acid and 4-aminoadamantane-1-carboxylic acid amide in the presence of a coupling reagent and an alkaline substance (See, Reaction Scheme 2):

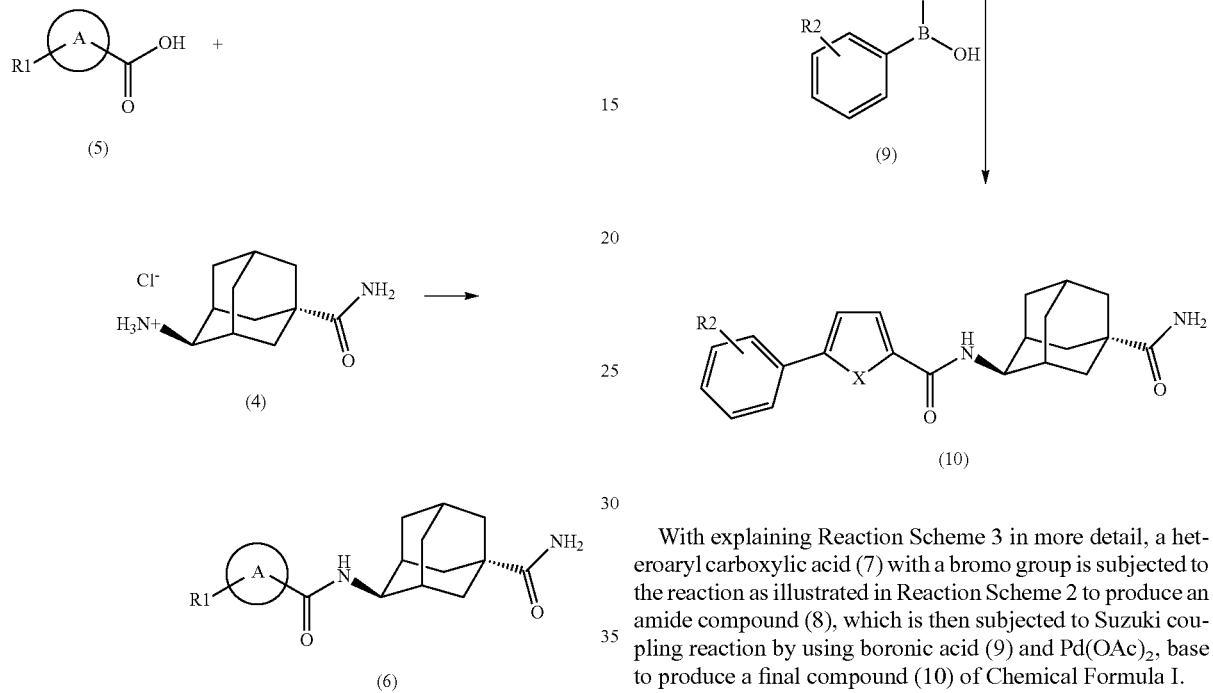

With explaining Reaction Scheme 2 in further detail, a coupling reagent (e.g., TBTU) and a base are added to a heteroaryl carboxylic acid (5) and 4-aminoadamantane-1-carboxylic acid amide (4) and the resulting mixture reacts to provide a final compound (6) of Chemical Compound I.

In another embodiment of the present invention, the production method may comprise the steps of preparing an amide compound from a heteroaryl carboxylic acid with a protective group via the reaction as illustrated in Reaction Scheme 2 and producing a final product of Chemical Formula I through Suzuki coupling (See, Reaction Scheme 3):

[Reaction Scheme 3]

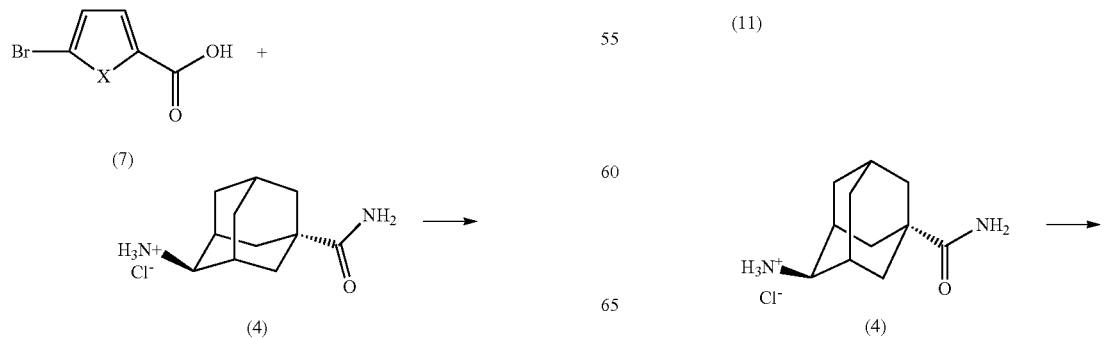

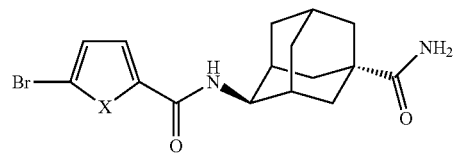

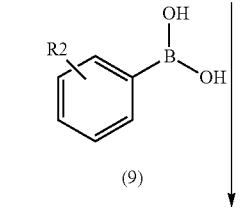

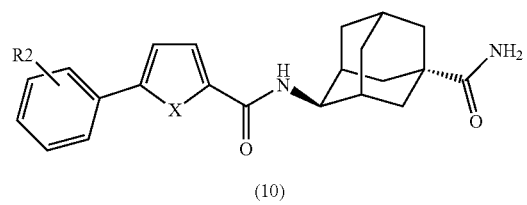

With explaining Reaction Scheme 3 in more detail, a heteroaryl carboxylic acid (7) with a bromo group is subjected to the reaction as illustrated in Reaction Scheme 2 to produce an amide compound (8), which is then subjected to Suzuki coupling reaction by using boronic acid (9) and Pd(OAc)$_2$, base to produce a final compound (10) of Chemical Formula I.

In another embodiment, the production method may comprise the steps of carrying out a reaction as illustrated in Reaction Scheme 2 with 6-hydroxy pyridine 2-carboxylic acid to prepare an amide compound and reacting the same with a reagent having a halide under an alkaline condition to prepare a compound of Chemical Formula I (See, Reaction Scheme 4)

[Reaction Scheme 4]

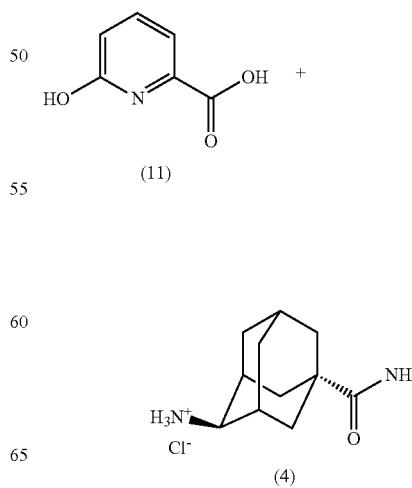

-continued

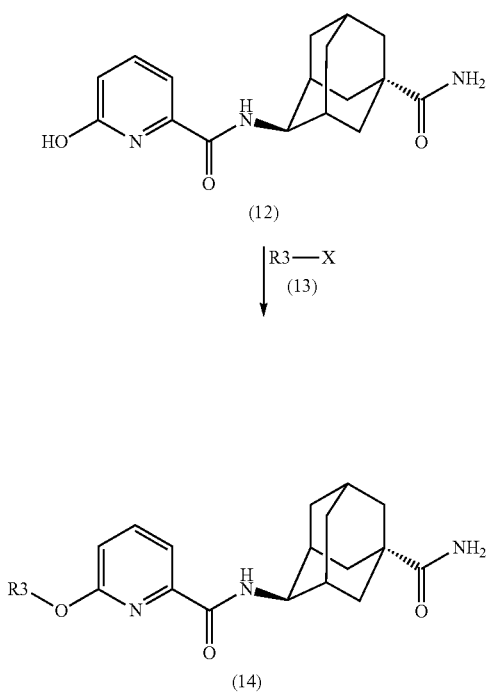

With explaining Reaction Scheme 4 in more detail, 6-hydroxy pyridine 2-carboxylic acid (11) is subjected to the reaction as illustrated in Reaction Scheme 2 to produce an amide compound (12), which is then reacted with a halide-containing reagent (13) to prepare a final compound (14) of Chemical Formula I.

In another embodiment, the production method may comprise the steps of carrying out the reaction as illustrated in Reaction Scheme 2 with 6-chloropyridine 2-carboxylic acid to prepare an amide compound (16) and reacting the same with an amine to be substituted by using microwaves to prepare a final product of Chemical Formula I (See, Reaction Scheme 5).

[Reaction Scheme 5]

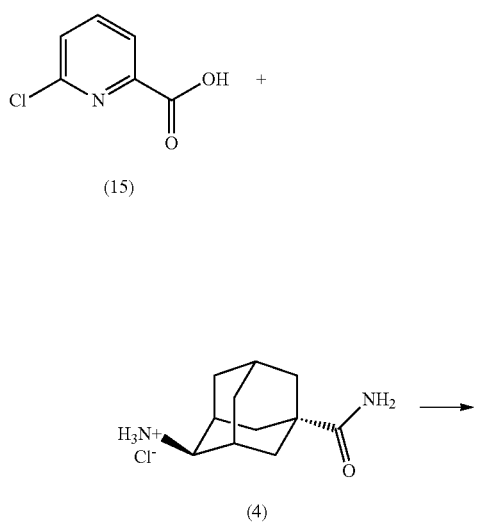

-continued

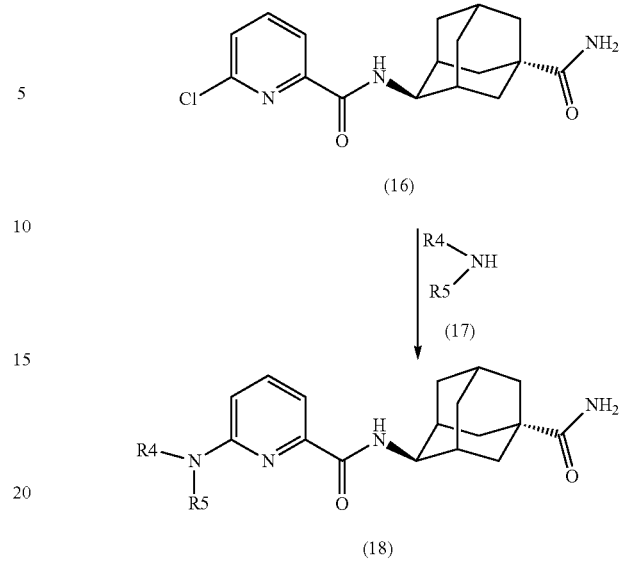

With explaining Reaction Scheme 5 in more detail, 6-chloropyridine 2-carboxylic acid (15) is subjected to the reaction as illustrated in Reaction Scheme 2 to provide an amide compound (16) and reacting the same with an amine (17) to be substituted in the presence of a DMSO solvent by using microwaves to prepare a final compound (18) of Chemical Formula I.

In another embodiments, the production method may comprise the steps of adding magnesium bis(monoperoxyphthalate) hexahydrate (MMPP) to a pyridine amide derivative and heating the resulting mixture to prepare a pyridine N-oxide compound (See, Reaction Scheme 6):

[Reaction Scheme 6]

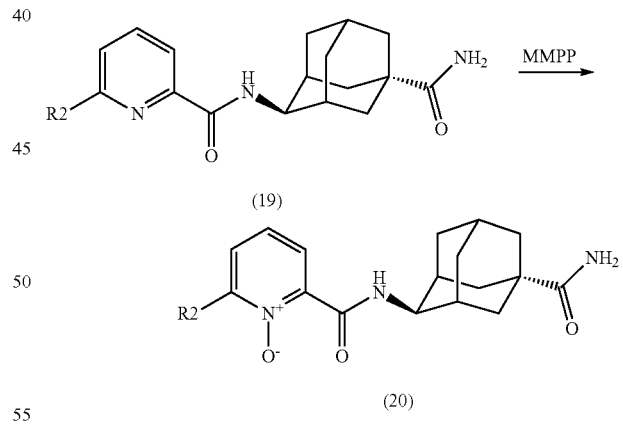

With explaining Reaction Scheme 6 in more detail, magnesium bis(monoperoxyphthalate) hexahydrate (MMPP) is added to a pyridine amide derivative (19) as synthesized in the manners as illustrated in Reaction Scheme 2, Reaction Scheme 4, and Reaction Scheme 5, and the resulting mixture is heated to 60° C. to provide a pyridine N-oxide compound (20).

In accordance with the present invention are provided a novel derivative of 5-carbamoyl adamantan-2-yl amide and a pharmaceutically acceptable salt thereof, which has an excellent effect of inhibiting 11b-HSD1. Therefore, the novel derivative of 5-carbamoyl adamantan-2-yl amide and the like may be effectively utilized for treatment and prevention of the diseases mediated by 11β-HSD1, including, for example, insulin dependent diabetes, non-insulin dependent diabetes, arthritis, obesity, metabolic syndrome, hypertension, hyperlipidemia, atherosclerosis, impaired glucose tolerance, and the like.

According to the present invention are also provided a method of producing the novel derivative of 5-carbamoyl adamantan-2-yl amide, a pharmaceutical composition comprising the same, and a method of inhibiting 11β-HSD1, and a method of treating diseases mediated by 11β-HSD1.

EXAMPLE

Hereinafter, the present invention will be described referring to the following examples. However, these examples are merely illustrative of the present invention, the scope of which shall not be limited thereto.

Preparation Example 1

Synthesis of (E) type of 4-aminoadamantane-1-carboxamide

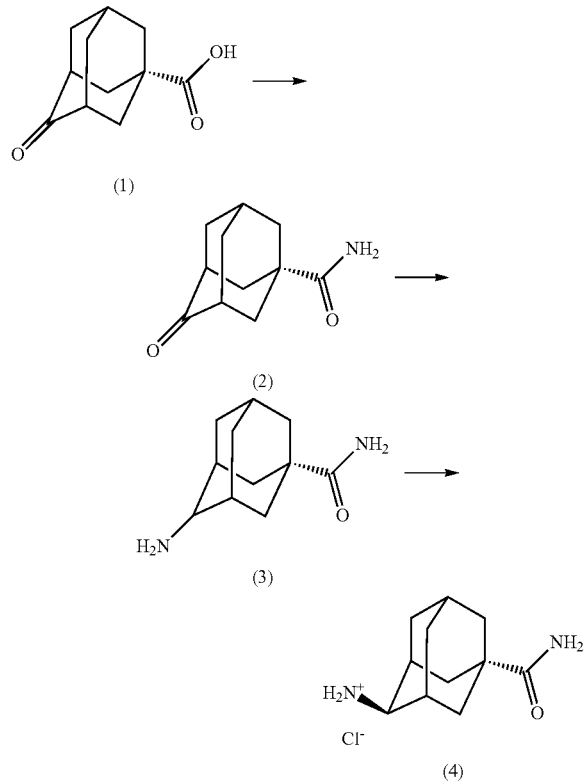

Step 1

50 g of 4-oxoadamantane-1-carboxylic acid (1) was dissolved in 300 mL of MC and to the resulting solution was slowly added dropwise 30 mL of oxalic chloride. Then, five drops of DMF were added and the resulting mixture was stirred at room temperature for two hours, distilled under a reduced pressure, and then vacuum-dried. The compound as vacuum-dried was dissolved in 150 mL of anhydrous THF and the resulting solution was added dropwise to a solution prepared by mixing 60 mL of ammonia water and 150 mL of THF. This reaction was extremely exothermic and thus the reactor cooled with iced water. After being stirred for 30 minutes, solids in the reaction product were filtered off by using MC, and the organic solution being collected was dried over $MgSO_4$ and then filtered and dried under a reduced pressure. The resulting product was recrystallized with a solution of MeOH and ether to provide 43 g of 4-oxoadamantane-1-carboxamide (2).

$^1$H-NMR ($CDCl_3$, 500 MHz) δ 5.58 (s, 1H), 5.47 (s, 1H), 2.63 (s, 2H), 2.21 (m, 5H), 2.12 (s, 2H), 2.04 (q, 4H)

Step 2

26 g of 4-oxoadamantane-1-carboxamide (2) was put into a sealed container and 190 mL of 7N $NH_3$ dissolved in MeOH was added thereto. Then, 1 g of a palladium catalyst (10 wt % Pd/C) was put into the reactor, and the reactor was filled with a nitrogen gas and the reactants were stirred for 18 hours. After the nitrogen gas was completely replaced with a hydrogen gas, the reactants were stirred for 24 hours and then filtered and distilled under a reduced pressure to provide a solid product. This solid product was placed and stirred in 100 mL of water and after the solids were removed therefrom, the remaining solution was distilled under a reduced pressure to provide 20 g of 4-aminoadamantane-1-carboxamide (3).

Step 3

20 g of 4-aminoadamantane-1-carboxamide (3) was dissolved in 10 mL of water and to the resulting solution, was added 10 mL of undiluted HCl to prepare a salt thereof. To the salt was added dropwise 260 mL of acetonitrile and stirred for 6 hours to produce a white solid product by filtration. This solid product was dissolved again in 20 mL of water and to the resulting solution was added dropwise 200 mL of acetonitrile and then stirred for 6 hours and filtered to prepare 9.5 g of (E) type of 4-aminoadamantane-1-carboxamide (4) as a white solid product.

$^1$H-NMR (DMSO-d6+$CDCl_3$, 500 MHz) δ 7.05 (s, 1H), 6.64 (s, 1H), 3.32 (s, 1H), 2.57 (s, 2H), 2.13 (s, 2H), 1.97 (m, 5H), 1.83 (s, 2H), 1.56 (d, 2H)

Preparation Example 2

Synthesis 5-bromo-N-(5-carbamoyl-2-adamantyl) furan-2-carboxamide

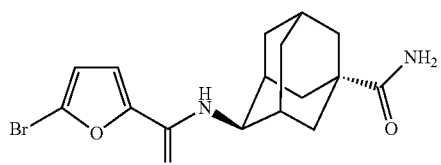

To a solution prepared by dissolving 100 mg of 5-bromofuran-2-carboxylic acid, 145 mg of (E) type 4-aminoadamantane-1-carboxylic acid amide (prepared from Preparation Example 1), and 202 mg of TBTU in MC was added dropwise 0.2 mL of DIEA and then stirred at room temperature for 4 hours. The reaction solution was washed with a 1N solution of HCl and a 1N solution of NaOH, respectively, and then washed again with brine. The resulting organic solution was dried over $MgSO_4$ and after filtration, was distilled under a reduced pressure. The compound thus obtained was purified via recrystallization by using MeOH and ether to produce 150 mg of a white solid product.

¹H-NMR (CDCl₃, 500 MHz) δ 7.07 (s, 1H), 6.51 (d, 1H), 6.45 (s, 1H), 5.59 (s, 1H), 5.27 (s, 1H), 4.20 (d, 1H), 2.18 (s, 2H), 2.09 (m, 5H), 1.94 (s, 2H), 1.91~1.66 (dd, 4H)

Preparation Example 3

Synthesis of 5-bromo-N-(5-carbamoyl-2-adamantyl)-1-methylpyrrole-2-carboxamide

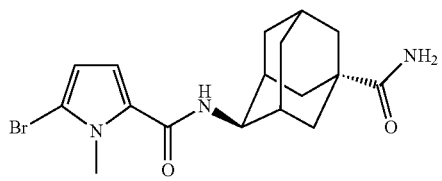

The title compound was synthesized in the same manner as synthesizing the title compound of Preparation Example 2 with using 5-bromo-1-methylpyrrole-2-carboxylic acid as a starting material (yield: 85%).
¹H-NMR (CDCl₃, 500 MHz) δ 6.55 (s, 1H), 6.18 (s, 1H), 6.09 (d, 1H), 5.57 (s, 1H), 5.24 (s, 1H), 4.14 (d, 1H), 3.92 (s, 3H), 2.15 (s, 2H), 2.06 (m, 5H), 1.92 (s, 2H), 1.84~1.64 (dd, 4H)

Preparation Example 4

Synthesis of 5-bromo-N-(5-carbamoyl-2-adamantyl)thiophene-2-carboxamide

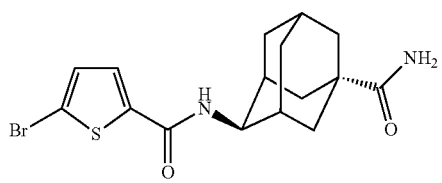 [SMILES: NC(=O)[C@]12CC3CC(C1)[C@@H](NC(=O)c1ccc(Br)s1)C(C3)C2]

The title compound was synthesized in the same manner as synthesizing the title compound of Preparation Example 2 with using 5-bromothiophene-2-carboxylic acid as a starting material (yield: 80%).
¹H-NMR (CDCl₃, 500 MHz) δ 7.24 (m, 1H), 7.05 (s, 1H), 6.08 (d, 1H), 5.57 (s, 1H), 5.19 (s, 1H), 4.28 (d, 1H), 2.19 (s, 2H), 2.08 (m, 5H), 1.94 (s, 2H), 1.84~1.66 (dd, 4H)

Preparation Example 5

Synthesis of N-(5-carbamoyl-2-adamantyl)-6-chloropyridine-2-carboxamide

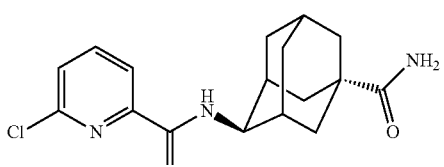

The title compound was synthesized in the same manner as synthesizing the title compound of Preparation Example 2 with using 6-chloropyridine-2-carboxylic acid as a starting material (yield: 89%).
¹H-NMR (CDCl3, 500 MHz) δ 8.20 (d, 1H), 8.13 (t, 1H), 7.82 (t, 1H), 7.47 (d, 1H), 5.59 (br, 1H), 5.27 (br, 1H), 4.22 (m, 1H), 2.22 (s, 2H), 2.12~1.95 (m, 7H), 1.68 (d, 2H)

Example 1

Synthesis of N-(5-carbamoyl-2-adamantyl)-5-phenylfuran-2-carboxamide (A: VII, X: O, R1: phenyl)

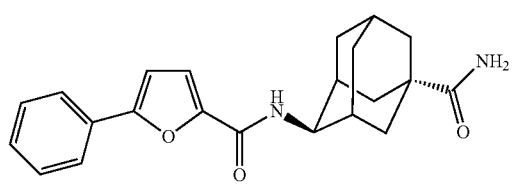 [SMILES: NC(=O)[C@]12CC3CC(C1)[C@@H](NC(=O)c1ccc(-c4ccccc4)o1)C(C3)C2]

The title compound was synthesized in the same manner as synthesizing the title compound of Preparation Example 2 with using 5-phenylfuran-2-carboxylic acid as a starting material (yield: 90%).
¹H-NMR (CDCl₃, 500 MHz) δ 7.71 (d, 2H), 7.46~7.43 (m, 2H), 7.37 (m, 1H), 7.19 (d, 1H), 6.75 (d, 1H), 6.66 (d, 1H), 5.62 (s, 91H), 5.34 (s, 1H), 2.22 (s, 2H), 2.13 (s, 1H), 2.08 (m, 4H), 1.96 (s, 2H), 1.93~1.70 (dd, 4H)

Example 2

Synthesis of N-(5-carbamoyl-2-adamantyl)-5-(4-chlorophenyl)furan-2-carboxamide (A: VII, X: O, R1: 4-chlorophenyl group)

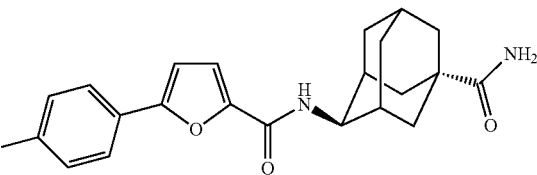

The title compound was synthesized in the same manner as synthesizing the title compound of Preparation Example 2 with using 5-(4-chlorophenyl)furan-2-carboxylic acid as a starting material (yield: 85%).

¹H-NMR (CDCl₃, 500 MHz) δ 7.63 (d, 2H), 7.42 (d, 2H), 7.19 (d, 1H), 6.74 (d, 1H), 6.62 (d, 1H), 5.60 (s, 1H), 5.24 (s, 1H), 2.22 (s, 2H), 2.13 (s, 1H), 2.08 (m, 4H), 1.96 (s, 2H), 1.93~1.70 (dd, 4H)

Example 3

Synthesis of N-(5-carbamoyl-2-adamantyl)-5-(4-nitrophenyl)furan-2-carboxamide (A: VII, X: O, R1: nitrophenyl)

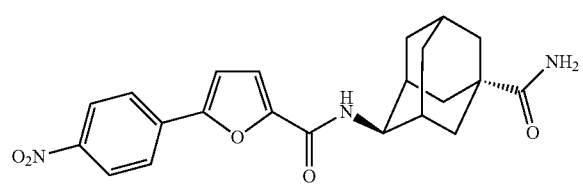 [SMILES: NC(=O)[C@]12CC3CC(C1)[C@@H](NC(=O)c1ccc(-c4ccc([N+](=O)[O-])cc4)o1)C(C3)C2]

The title compound was synthesized in the same manner as synthesizing the title compound of Preparation Example 2 with using 5-(4-nitrophenyl)furan-2-carboxylic acid as a starting material (yield: 90%).

¹H-NMR (CDCl₃, 500 MHz) δ 8.32 (d, 2H), 7.90 (d, 2H), 7.24 (s, 1H), 7.01 (s, 1H), 6.81 (d, 1H), 6.15 (s, 1H), 5.79 (s, 1H), 4.24 (d, 1H), 2.59 (m, 1H), 2.23 (s, 2H), 2.13 (m, 5H), 1.95 (m, 4H), 1.70 (d, 2H)

Example 4

Synthesis of N-(5-carbamoyl-2-adamantyl)-5-(4-methylphenyl)furan-2-carboxamide (A: VII, X: O, R1: methylphenyl group)

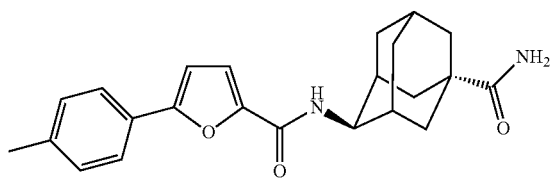 [SMILES: Cc1ccc(-c2ccc(C(=O)N[C@H]3C4CC5CC3C[C@](C(N)=O)(C5)C4)o2)cc1]

The title compound was synthesized in the same manner as synthesizing the title compound of Preparation Example 2 with using 5-(4-methylphenyl)furan-2-carboxylic acid as a starting material (yield: 90%).

¹H-NMR (CDCl₃, 500 MHz) δ 7.59 (d, 2H), 7.23 (d, 2H), 7.18 (s, 1H), 6.68 (s, 1H), 6.65 (d, 1H), 5.59 (s, 1H), 5.22 (s, 1H), 4.25 (d, 1H), 2.39 (s, 3H), 2.23 (s, 2H), 2.09 (m, 5H), 1.96 (m, 4H), 1.69 (d, 2H)

Example 5

Synthesis of 5-t-butyl-N-(5-carbamoyl-2-adamantyl)-1,2-oxazole-3-carboxamide (A: VIII, R1: a C3 branched alkyl group)

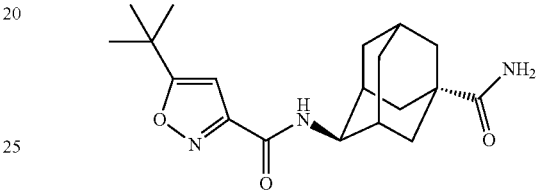

The title compound was synthesized in the same manner as synthesizing the title compound of Preparation Example 2 with using 5-t-butyl-isoxazole-3-carboxylic acid as a starting material (yield: 83%).

¹H-NMR (CDCl₃, 500 MHz) δ 7.07 (d, 1H), 6.42 (s, 1H), 5.58 (s, 1H), 5.25 (s, 1H), 4.22 (d, 1H), 2.20 (s, 2H), 2.09 (m, 5H), 1.94 (s, 2H), 1.92~1.65 (dd, 4H), 1.38 (s, 9H)

Example 6

Synthesis of N-(5-carbamoyl-2-adamantyl)-5-(3-methylphenyl)-1,2-oxazole-3-carboxamide (A: VIII, R1: 3-methylphenyl group)

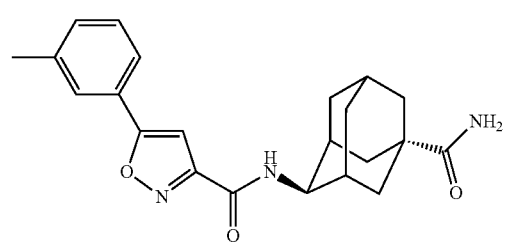 [SMILES: Cc1cccc(-c2cc(C(=O)N[C@H]3C4CC5CC3C[C@](C(N)=O)(C5)C4)no2)c1]

The title compound was synthesized in the same manner as synthesizing the title compound of Preparation Example 2 with using 5-(3-methylphenyl)-isoxazole-3-carboxylic acid as a starting material (yield: 85%).

¹H-NMR (CDCl₃, 500 MHz) δ 7.62 (m, 2H), 7.39 (t, 1H), 7.31 (m, 1H), 7.13 (d, 1H), 6.95 (s, 1H), 6.42 (s, 1H), 5.59 (s,

1H), 5.20 (s, 1H), 4.26 (d, 1H), 2.44 (s, 3H), 2.23 (s, 2H), 2.11 (m, 7H), 1.96 (s, 2H), 1.93~1.55 (dd, 4H)

Example 7

Synthesis of N-(5-carbamoyl-2-adamantyl)-5-(2-methoxyphenyl)-1,2-oxazole-3-carboxamide (A: VIII, R1: 2-methoxyphenyl group)

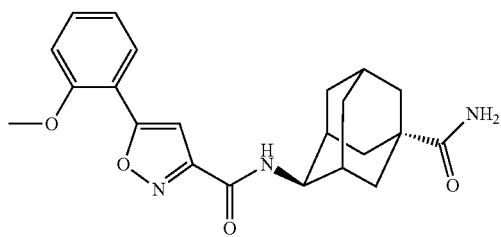 [SMILES: COc1ccccc1-c1cc(C(=O)N[C@H]2C3CC4CC2C[C@](C(N)=O)(C4)C3)no1]

The title compound was synthesized in the same manner as synthesizing the title compound of Preparation Example 2 with using 5-(2-methoxyphenyl)-isoxazole-3-carboxylic acid as a starting material (yield: 80%).

$^1$H-NMR (CDCl$_3$, 500 MHz) δ 7.97 (d, 1H), 7.45 (t, 1H), 7.23 (s, 1H), 7.16 (d, 1H), 7.10 (t, 1H), 7.05 (d, 1H), 5.59 (s, 1H), 5.24 (s, 1H), 4.27 (d, 1H), 3.98 (s, 3H), 2.24 (s, 2H), 2.10 (m, 5H), 1.95 (m, 4H), 1.68 (d, 2H)

Example 8

Synthesis of N-(5-carbamoyl-2-adamantyl)-5-(2-methylphenyl)-1,2-oxazole-3-carboxamide (A: VIII, R1: 2-methylphenyl group)

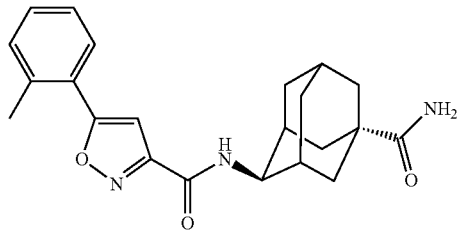 [SMILES: Cc1ccccc1-c1cc(C(=O)N[C@H]2C3CC4CC2C[C@](C(N)=O)(C4)C3)no1]

The title compound was synthesized in the same manner as synthesizing the title compound of Preparation Example 2 with using 5-(2-methylphenyl)-isoxazole-3-carboxylic acid as a starting material (yield: 78%).

$^1$H-NMR (CDCl$_3$, 500 MHz) δ 7.74 (d, 1H), 7.38 (d, 1H), 7.34 (m, 2H), 7.16 (d, 1H), 6.89 (s, 1H), 5.59 (s, 1H), 5.20 (s, 1H), 4.27 (d, 1H), 2.54 (s, 3H), 2.24 (s, 2H), 2.11 (m, 5H), 1.96 (m, 4H), 1.69 (d, 2H)

Example 9

Synthesis of N-(5-carbamoyl-2-adamantyl)-5-(3-methoxyphenyl)-1,2-oxazole-3-carboxamide (A: VIII, R1: 3-methoxyphenyl group)

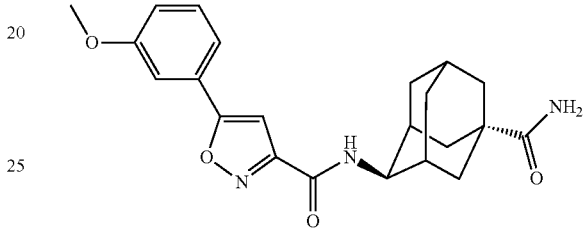

The title compound was synthesized in the same manner as synthesizing the title compound of Preparation Example 2 with using 5-(3-methoxyphenyl)-isoxazole-3-carboxylic acid as a starting material (yield: 83%).

$^1$H-NMR (CDCl$_3$, 500 MHz) δ 7.41 (m, 2H), 7.33 (s, 1H), 7.13 (d, 1H), 7.03 (m, 1H), 6.96 (s, 1H), 5.59 (s, 1H), 5.21 (s, 1H), 4.26 (d, 1H), 3.89 (s, 3H), 2.24 (s, 2H), 2.11 (m, 5H), 1.96 (m, 4H), 1.69 (d, 2H)

Example 10

Synthesis of N-(5-carbamoyl-2-adamantyl)-5-(furan-3-yl)-1,2-oxazole-3-carboxamide (A: VIII, R1: furan)

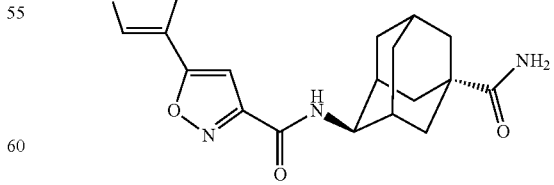

The title compound was synthesized in the same manner as synthesizing the title compound of Preparation Example 2 with using 5-(furan-3-yl)-isoxazole-3-carboxylic acid as a starting material (yield: 85%).

¹H-NMR (CDCl₃, 500 MHz) δ 7.96 (s, 1H), 7.54 (s, 1H), 7.10 (d, 1H), 6.74 (s, 1H), 6.72 (s, 1H), 5.58 (s, 1H), 5.24 (s, 1H), 4.24 (d, 1H), 3.89 (s, 3H), 2.22 (s, 2H); 2.10 (m, 5H), 1.94 (m, 4H), 1.68 (d, 2H)

Example 11

Synthesis of N-(5-carbamoyl-2-adamantyl)-5-(thiophen-3-yl)-1,2-oxazole-3-carboxamide (A: VIII, R1: thiophene)

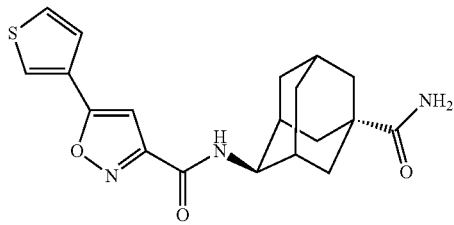 [SMILES: NC(=O)[C@]12CC3CC(C1)[C@@H](NC(=O)c1cc(-c4ccsc4)on1)C(C3)C2]

The title compound was synthesized in the same manner as synthesizing the title compound of Preparation Example 2 with using 5-(thiophen-3-yl)-isoxazole-3-carboxylic acid as a starting material (yield: 86%).

¹H-NMR (CDCl₃, 500 MHz) δ 7.84 (s, 1H), 7.45 (m, 2H), 7.12 (d, 1H), 6.82 (s, 1H), 5.59 (s, 1H), 5.25 (s, 1H), 4.25 (d, 1H), 2.23 (s, 2H), 2.11 (m, 5H), 1.95 (m, 4H), 1.68 (d, 2H)

Example 12

Synthesis of N-(5-carbamoyl-2-adamantyl)-5-(3-fluorophenyl)-1,2-oxazole-3-carboxamide (A: VIII, R1: 3-fluorophenyl group)

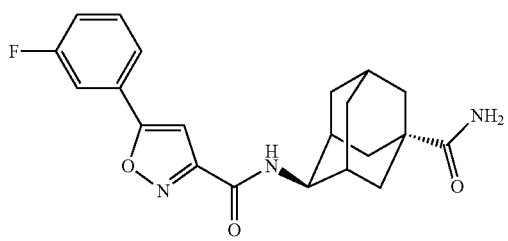 [SMILES: NC(=O)[C@]12CC3CC(C1)[C@@H](NC(=O)c1cc(-c4cccc(F)c4)on1)C(C3)C2]

The title compound was synthesized in the same manner as synthesizing the title compound of Preparation Example 2 with using 5-(3-fluorophenyl)-isoxazole-3-carboxylic acid as a starting material (yield: 90%).

¹H-NMR (CDCl₃, 500 MHz) δ 7.62 (d, 1H), 7.50 (m, 2H), 7.28 (d, 1H), 7.18 (m, 1H), 7.05 (s, 1H), 6.41 (s, 1H), 6.01 (s, 1H), 4.22 (d, 1H), 2.65 (s, 1H), 2.59 (s, 1H), 2.20 (s, 2H), 2.05 (m, 5H), 1.95 (m, 4H), 1.65 (d, 2H)

Example 13

Synthesis of N-(5-carbamoyl-2-adamantyl)-5-(4-chlorophenyl)-1,2-oxazole-3-carboxamide (A: VIII, R1: 4-chlorophenyl group)

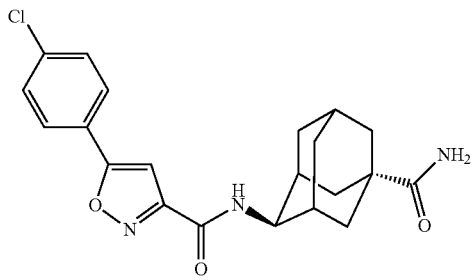 [SMILES: NC(=O)[C@]12CC3CC(C1)[C@@H](NC(=O)c1cc(-c4ccc(Cl)cc4)on1)C(C3)C2]

The title compound was synthesized in the same manner as synthesizing the title compound of Preparation Example 2 with using 5-(3-chlorophenyl)-isoxazole-3-carboxylic acid as a starting material (yield: 90%).

¹H-NMR (CDCl₃, 500 MHz) δ 7.74 (d, 2H), 7.11 (d, 2H), 6.95 (s, 1H), 5.59 (s, 1H), 5.30 (s, 1H), 4.24 (d, 1H), 2.22 (s, 2H), 2.09 (m, 5H), 1.94 (m, 4H), 1.68 (d, 2H)

Example 14

Synthesis of N-(5-carbamoyl-2-adamantyl)-5-(2-methyl-1,3-thiazol-4-yl)-1,2-oxazole-3-carboxamide (A: VIII, R1: methyl thiazole group)

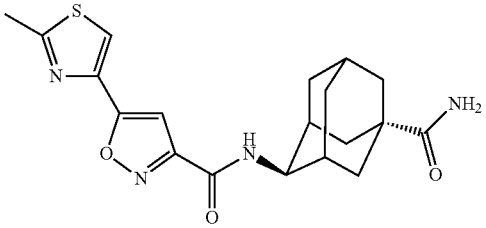 [SMILES: Cc1nc(-c2cc(C(=O)N[C@H]3C4CC5CC3C[C@](C(N)=O)(C5)C4)no2)cs1]

The title compound was synthesized in the same manner as synthesizing the title compound of Preparation Example 2 with using 5-(2-methyl-1,3-thiazol-4-yl)-isoxazole-3-carboxylic acid as a starting material (yield: 78%).

¹H-NMR (CDCl₃, 500 MHz) δ 7.70 (s, 1H), 7.10 (d, 1H), 7.06 (s, 1H), 5.58 (s, 1H), 5.23 (s, 1H), 4.24 (d, 1H), 2.78 (s, 3H), 2.23 (s, 2H), 2.10 (m, 5H), 1.94 (m, 4H), 1.68 (d, 2H)

Example 15

Synthesis of N-(5-carbamoyl-2-adamantyl)-6-methylpyridine-2-carboxamide (A: II, R1: methyl group)

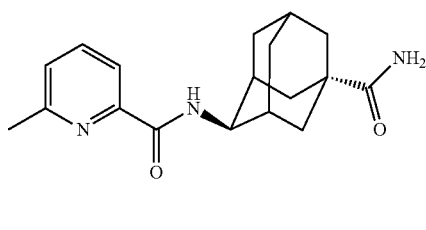 [SMILES: Cc1cccc(C(=O)N[C@H]2C3CC4CC2C[C@](C(N)=O)(C4)C3)n1]

The title compound was synthesized in the same manner as synthesizing the title compound of Preparation Example 2 with using 6-methylpyridine-2-carboxylic acid as a starting material (yield: 78%).

¹H-NMR (CDCl₃, 500 MHz) δ 8.71 (d, 1H), 8.32 (s, 2H), 8.15 (d, 1H), 7.90 (d, 1H), 7.79 (m, 1H), 7.65 (m, 1H), 5.63 (s, 1H), 5.36 (s, 1H), 4.30 (d, 1H), 2.29 (s, 2H), 2.15 (m, 7H), 1.98 (s, 2H), 1.72 (d, 2H)

Example 16

Synthesis of N-(5-carbamoyl-2-adamantyl)pyridine-2-carboxamide (A: II, R1: H)

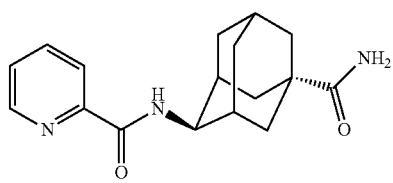 [SMILES: NC(=O)[C@]12CC3CC(C1)[C@@H](NC(=O)c1ccccn1)C(C3)C2]

The title compound was synthesized in the same manner as synthesizing the title compound of Preparation Example 2 with using pyridine-2-carboxylic acid as a starting material (yield: 80%).

¹H-NMR (CDCl₃, 500 MHz) δ 8.57 (s, 1H), 8.50 (d, 1H), 8.20 (d, 2H), 7.85 (t, 1H), 7.43 (m, 2H), 5.66 (s, 1H), 5.54 (s, 1H), 4.25 (d, 1H), 2.21 (s, 2H), 2.10~1.94 (m, 9H), 1.66 (d, 2H)

Example 17

Synthesis of N-(5-carbamoyl-2-adamantyl)-1-methylpyrrole-2-carboxamide (A: VII, X: N—Y, Y: methyl group, R1: H)

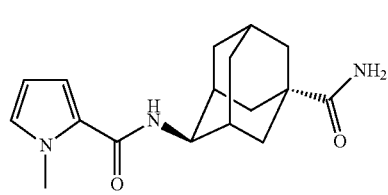 [SMILES: Cn1cccc1C(=O)N[C@H]1C2CC3CC1C[C@](C(N)=O)(C3)C2]

The title compound was synthesized in the same manner as synthesizing the title compound of Preparation Example 2 with using 1-methylpyrrole-2-carboxylic acid as a starting material (yield: 85%).

¹H-NMR (CDCl₃, 500 MHz) δ 6.72 (s, 1H), 6.55 (d, 1H), 6.14 (d, 1H), 6.09 (m, 1H), 5.56 (s, 1H), 5.20 (s, 1H), 4.16 (d, 1H), 3.93 (s, 3H), 2.16 (s, 2H), 2.06 (m, 5H), 1.93 (s, 2H), 1.86~1.64 (dd, 4H)

Example 18

Synthesis N-(5-carbamoyl-2-adamantyl)quinoline-2-carboxamide (A: III, R1: H)

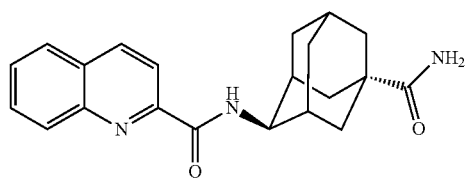 [SMILES: NC(=O)[C@]12CC3CC(C1)[C@@H](NC(=O)c1ccc4ccccc4n1)C(C3)C2]

The title compound was synthesized in the same manner as synthesizing the title compound of Preparation Example 2 with using quinoline-2-carboxylic acid as a starting material (yield: 93%).

¹H-NMR (CDCl₃, 500 MHz) δ 8.60 (d, 1H), 8.00 (d, 1H), 7.70 (t, 1H), 7.28 (d, 1H), 5.65 (s, 1H), 5.45 (s, 1H), 4.23 (d, 1H), 2.59 (s, 3H), 2.21 (s, 2H), 2.09 (m, 5H), 1.98 (s, 2H), 1.88~1.66 (dd, 4H)

Example 19

Synthesis of N-(5-carbamoyl-2-adamantyl)quinoline-8-carboxamide (A: IV, R1: H)

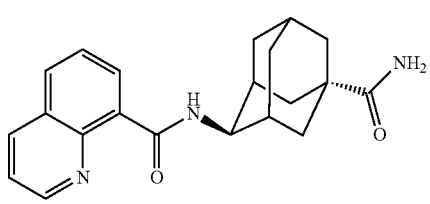 [SMILES: NC(=O)[C@]12CC3CC(C1)[C@@H](NC(=O)c1cccc4cccnc14)C(C3)C2]

The title compound was synthesized in the same manner as synthesizing the title compound of Preparation Example 2 with using quinoline-8-carboxylic acid as a starting material (yield: 87%).

1H-NMR (CDCl3, 500 MHz) δ 11.90 (d, 1H), 8.95 (d, 1H), 8.88 (d, 1H), 8.29 (t, 1H), 7.96 (d, 1H), 7.69 (t, 1H), 7.50 (t, 1H), 5.65 (br, 1H), 5.30 (br, 1H), 4.43 (m, 1H), 2.34~4.92 (m, 11H), 1.70 (d, 2H)

Example 20

Synthesis of N-(5-carbamoyl-2-adamantyl)-8-hydroxyquinoline-2-carboxamide (A: VIII, R1: hydroxy group)

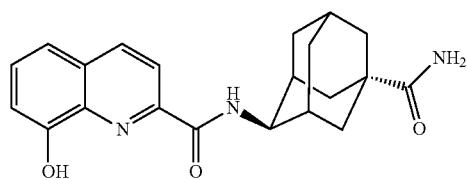 [SMILES: NC(=O)[C@]12CC3CC(C1)[C@@H](NC(=O)c1ccc4cccc(O)c4n1)C(C3)C2]

The title compound was synthesized in the same manner as synthesizing the title compound of Preparation Example 2 with using 8-hydroxyquinoline-2-carboxylic acid as a starting material (yield: 85%).

¹H-NMR (CDCl₃, 500 MHz) δ 8.35 (s, 2H), 8.20 (d, 1H), 7.67 (s, 1H), 7.56 (d, 1H), 7.43 (d, 1H), 7.26 (m, 1H), 5.64 (s, 1H), 5.38 (s, 1H), 4.31 (d, 1H), 2.29 (s, 2H), 2.12 (m, 5H), 1.98 (m, 4H), 1.74 (d, 2H)

Example 21

Synthesis of N-(5-carbamoyl-2-adamantyl)-5-thiophen-2-yl-thiophene-2-carboxamide (A: VII, X: S, R1: thiophene group)

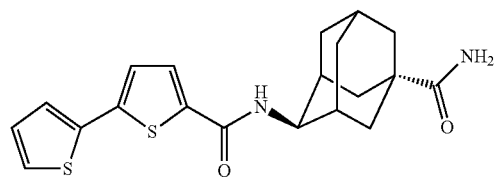 [SMILES: NC(=O)[C@]12CC3CC(C1)[C@@H](NC(=O)c1ccc(-c4cccs4)s1)C(C3)C2]

The title compound was synthesized in the same manner as synthesizing the title compound of Preparation Example 2 with using [2,2']bithiophenyl-5-carboxylic acid as a starting material (yield: 90%).

¹H-NMR (CDCl₃, 500 MHz) δ 7.42 (d, 1H), 7.29 (m, 1H), 7.13 (d, 1H), 7.04 (m, 1H), 6.15 (d, 1H), 5.59 (s, 1H), 5.23 (s, 1H), 5.16 (s, 2H), 4.22 (d, 1H), 2.21 (s, 2H), 2.05 (m, 5H), 1.94 (s, 2H), 1.88~1.67 (dd, 4H)

Example 22

Synthesis of N-(5-carbamoyl-2-adamantyl)thiophene-2-carboxamide (A: VII, X: S, R1: H)

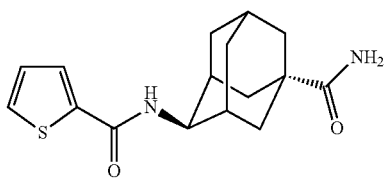 [SMILES: NC(=O)[C@]12CC3CC(C1)[C@@H](NC(=O)c1cccs1)C(C3)C2]

The title compound was synthesized in the same manner as synthesizing the title compound of Preparation Example 2 with using thiophene-2-carboxylic acid as a starting material (yield: 87%).

¹H-NMR (CDCl₃, 500 MHz) δ 7.53~7.48 (m, 2H), 7.10 (m, 1H), 6.21 (d, 1H), 5.65 (s, 1H), 5.38 (s, 1H), 4.22 (d, 1H), 2.22 (s, 2H), 2.09 (m, 5H), 1.95 (s, 2H), 1.88~1.67 (dd, 4H)

Example 23

Synthesis of N-(5-carbamoyl-2-adamantyl)-4-methylthiophene-2-carboxamide (A: VII, X: S, R1: 4-methyl group)

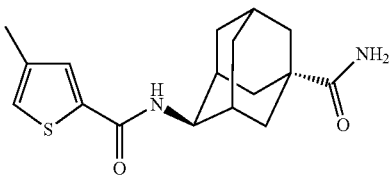 [SMILES: Cc1csc(C(=O)N[C@H]2C3CC4CC2C[C@](C(N)=O)(C4)C3)c1]

The title compound was synthesized in the same manner as synthesizing the title compound of Preparation Example 2 with using 4-methylthiophene-2-carboxylic acid as a starting material (yield: 87%).

¹H-NMR (CDCl₃, 500 MHz) δ 8.10~8.00 (m, 1H), 7.57~7.47 (m, 2H), 7.33 (s, 1H), 7.06 (s, 1H), 6.16 (d, 1H), 5.58 (s, 1H), 5.20 (s, 1H), 4.21 (d, 1H), 2.30 (s, 3H), 2.21 (s, 2H), 2.09 (m, 5H), 1.95 (s, 2H), 1.88~1.67 (dd, 4H)

Example 24

Synthesis of N-(5-carbamoyl-2-adamantyl)-5-methylthiophene-2-carboxamide (A: VII, X: S, R1: 5-methyl group)

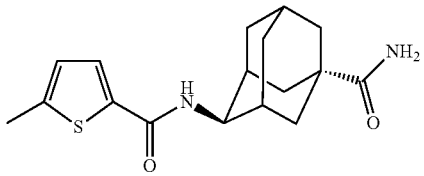 [SMILES: Cc1ccc(C(=O)N[C@H]2C3CC4CC2C[C@](C(N)=O)(C4)C3)s1]

The title compound was synthesized in the same manner as synthesizing the title compound of Preparation Example 2 with using 5-methylthiophene-2-carboxylic acid as a starting material (yield: 89%).

¹H-NMR (CDCl₃, 500 MHz) δ 7.35 (d, 1H), 6.74 (d, 1H), 6.28 (m, 1H), 5.97 (s, 1H), 5.62 (s, 1H), 4.17 (d, 1H), 2.58 (s, 3H), 2.17 (s, 2H), 2.04 (m, 5H), 1.91 (s, 2H), 1.88~1.63 (dd, 4H)

Example 25

Synthesis of N-(5-carbamoyl-2-adamantyl)-5-(4-fluorophenyl)furan-2-carboxamide (A: VII, X: O, R1: fluorophenyl group)

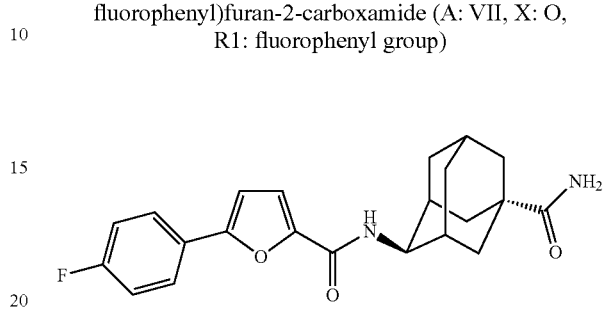

100 mg of 5-bromo-N-(5-carbamoyl-2-adamantyl)furan-2-carboxamide (Example 8) and 100 mg of 4-fluorophenyl-boronic acid, 10 mg of palladium acetate (Pd(OAc)₂), 130 mg of K₂CO₃, 25 mg of tri(o-tolyl)phosphine, and 100 mg of tetrabutylammonium bromide ("Bu4NBr) were dissolved in 2 mL of toluene, 2 mL of methanol, and 1 mL of water and then stirred at 75° C. for 12 hours. After the completion of the reaction was confirmed via HPLC, 10 mL of ethyl acetate (EA) was put into the reaction solution, which was then neutralized with a 1N solution of HCl. After being filtered through Celite, the reaction product was separated into an organic solvent layer and a water layer. The organic solvent layers as collected were dried over MgSO₄, and then filtered and distilled under a reduced pressure to produce the title product. The product thus obtained was purified through a tube chromatography (MC:MeOH=19:1, (v/v)) and then finally through prep LC to produce 50 mg of a white solid product.

¹H-NMR (CDCl₃, 500 MHz) δ 7.67 (dd, 2H), 7.17 (s, 1H), 7.14 (m, 1H), 6.69 (s, 1H), 6.62 (m, 1H), 5.58 (s, 1H), 5.21 (s, 1H), 4.25 (d, 1H), 2.23 (s, 2H), 2.07 (m, 5H), 1.96 (s, 2H), 1.93~1.69 (dd, 4H)

Example 26

Synthesis of N-(5-carbamoyl-2-adamantyl)-5-(3-chlorophenyl)furan-2-carboxamide (A: VII, X: O, R1: 3-chlorophenyl group)

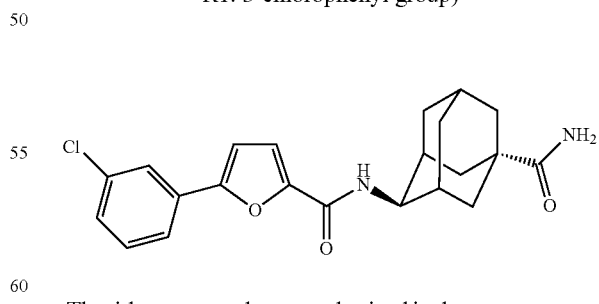

The title compound was synthesized in the same manner as synthesizing the title compound of Example 25 with using 5-bromo-N-(5-carbamoyl-2-adamantyl)furan-2-carboxamide (from Preparation Example 2) and 3-chlorophenyl boronic acid as a starting material (yield: 85%).

¹H-NMR (CDCl₃, 500 MHz) δ 7.67 (s, 1H), 7.58 (d, 1H), 7.37 (t, 1H), 7.33 (m, 1H), 7.19 (s, 1H), 6.77 (s, 1H), 6.63 (d,

1H), 5.59 (s, 1H), 5.22 (s, 1H), 4.25 (d, 1H), 2.24 (s, 2H), 2.09 (m, 5H), 1.96 (m, 4H), 1.70 (d, 2H)

Example 27

Synthesis of N-(5-carbamoyl-2-adamantyl)-5-(2-chlorophenyl)furan-2-carboxamide (A: VII, X: O, R1: 2-chlorophenyl group)

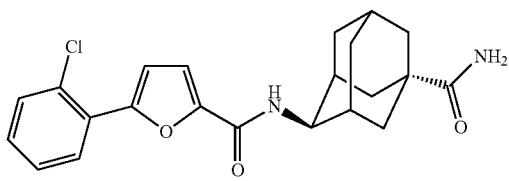 [SMILES: NC(=O)[C@]12CC3CC(C1)[C@@H](NC(=O)c1ccc(-c4ccccc4Cl)o1)C(C3)C2]

The title compound was synthesized in the same manner as synthesizing the title compound of Example 25 with using 5-bromo-N-(5-carbamoyl-2-adamantyl)furan-2-carboxamide (from Preparation Example 2) and 2-chlorophenyl boronic acid as a starting material (yield: 87%).

$^1$H-NMR (CDCl$_3$, 500 MHz) δ 7.77 (d, 1H), 7.50 (d, 1H), 7.37 (t, 1H), 7.31 (m, 1H), 7.21 (s, 1H), 7.10 (s, 1H), 6.70 (d, 1H), 5.58 (s, 1H), 5.20 (s, 1H), 4.26 (d, 1H), 2.22 (s, 2H), 2.10 (m, 5H), 1.95 (s, 2H), 1.92~1.68 (dd, 4H)

Example 28

Synthesis of N-(5-carbamoyl-2-adamantyl)-5-(4-methoxyphenyl)furan-2-carboxamide (A: VII, X: O, R1: 4-methoxyphenyl group)

The title compound was synthesized in the same manner as synthesizing the title compound of Example 25 with using 5-bromo-N-(5-carbamoyl-2-adamantyl)furan-2-carboxamide (from Preparation Example 2) and 4-methoxyphenyl boronic acid as a starting material (yield: 85%).

$^1$H-NMR (CDCl$_3$, 500 MHz) δ 7.63 (d, 2H), 7.17 (s, 1H), 6.97 (d, 2H), 6.63 (d, 1H), 6.61 (s, 1H), 5.59 (s, 1H), 5.22 (s, 1H), 4.23 (d, 1H), 3.86 (s, 3H), 2.22 (s, 2H), 2.09 (m, 5H), 1.95 (s, 2H), 1.91~1.69 (dd, 4H)

Example 29

Synthesis of N-(5-carbamoyl-2-adamantyl)-5-(3,4-difluorophenyl)furan-2-carboxamide (A: VII, X: O, R1: 3,4-difluorophenyl group)

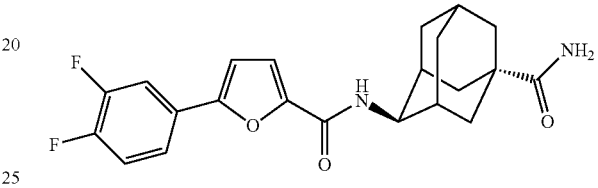

The title compound was synthesized in the same manner as synthesizing the title compound of Example 25 with using 5-bromo-N-(5-carbamoyl-2-adamantyl)furan-2-carboxamide (from Preparation Example 2) and 3,4-difluorophenyl boronic acid as a starting material (yield: 90%).

$^1$H-NMR (CDCl$_3$, 500 MHz) δ 7.49 (m, 1H), 7.43 (m, 1H), 7.24 (m, 1H), 7.18 (s, 1H), 6.70 (s, 1H), 6.60 (d, 1H), 5.59 (s, 1H), 5.24 (s, 1H), 4.25 (d, 1H), 2.22 (s, 2H), 2.09 (m, 5H), 1.96 (s, 2H), 1.93~1.70 (dd, 4H)

Example 30

Synthesis of N-(5-carbamoyl-2-adamantyl)-5-(2-fluorophenyl)furan-2-carboxamide (A: VII, X: O, R1: 2-fluorophenyl group)

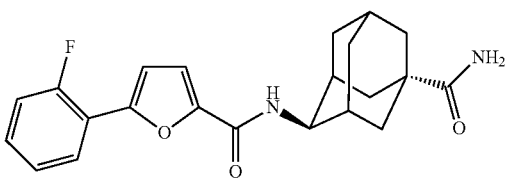

The title compound was synthesized in the same manner as synthesizing the title compound of Example 25 with using 5-bromo-N-(5-carbamoyl-2-adamantyl)furan-2-carboxamide (from Preparation Example 2) and 2-fluorophenyl boronic acid as a starting material (yield: 90%).

$^1$H-NMR (CDCl$_3$, 500 MHz) δ 7.80 (t, 1H), 7.34 (m, 1H), 7.17 (m, 1H), 7.15 (m, 1H), 6.93 (s, 1H), 6.67 (d, 1H), 5.60 (s,

1H), 5.24 (s, 1H), 4.25 (d, 1H), 2.23 (s, 2H), 2.12 (m, 5H), 1.99 (s, 2H), 1.94~1.70 (dd, 4H)

Example 31

Synthesis of N-(5-carbamoyl-2-adamantyl)-5-(3,4-dichlorophenyl)furan-2-carboxamide (A: VII, X: O, R1: 3,4-dichlorophenyl group)

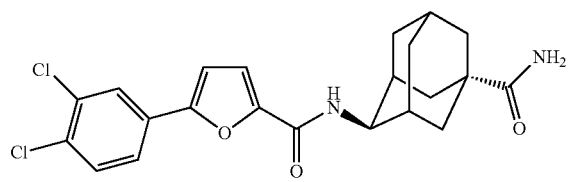 [SMILES: NC(=O)[C@]12CC3CC(C1)[C@@H](NC(=O)c1ccc(-c4ccc(Cl)c(Cl)c4)o1)C(C3)C2]

The title compound was synthesized in the same manner as synthesizing the title compound of Example 25 with using 5-bromo-N-(5-carbamoyl-2-adamantyl)furan-2-carboxamide (from Preparation Example 2) and 3,4-dichlorophenyl boronic acid as a starting material (yield: 83%).

$^1$H-NMR (CDCl$_3$, 500 MHz) δ 7.76 (s, 1H), 7.51 (s, 2H), 7.19 (s, 1H), 6.77 (s, 1H), 6.60 (d, 1H), 5.59 (s, 1H), 5.21 (s, 1H), 4.25 (d, 1H), 2.24 (s, 2H), 2.13 (s, 1H), 2.07 (q, 4H), 1.96 (s, 2H), 1.93~1.70 (dd, 4H)

Example 32

Synthesis of N-(5-carbamoyl-2-adamantyl)-5-(3,5-dichlorophenyl)furan-2-carboxamide (A: VII, X: O, R1: 3,5-difluorophenyl group)

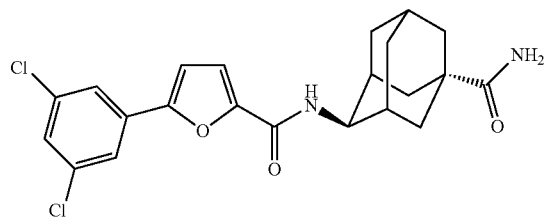 [SMILES: NC(=O)[C@]12CC3CC(C1)[C@@H](NC(=O)c1ccc(-c4cc(Cl)cc(Cl)c4)o1)C(C3)C2]

The title compound was synthesized in the same manner as synthesizing the title compound of Example 25 with using 5-bromo-N-(5-carbamoyl-2-adamantyl)furan-2-carboxamide (from Preparation Example 2) and 3,5-dichlorophenyl boronic acid as a starting material (yield: 85%).

$^1$H-NMR (CDCl$_3$, 500 MHz) δ 7.55 (s, 2H), 7.34 (s, 1H), 7.20 (s, 1H), 6.80 (s, 1H), 6.59 (d, 1H), 5.58 (s, 1H), 5.19 (s, 1H), 4.24 (d, 1H), 2.24 (s, 2H), 2.14 (s, 1H), 2.07 (q, 4H), 1.96 (s, 2H), 1.94~1.70 (dd, 4H)

Example 33

Synthesis of N-(5-carbamoyl-2-adamantyl)-5-(3-chlorophenyl)-1-methylpyrrole-2-carboxamide (A: VII, X: N—Y, Y: methyl group, R1: 3-chlorophenyl group)

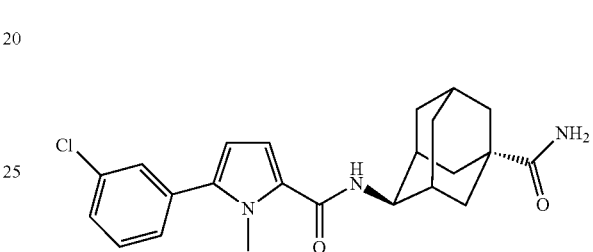

The title compound was synthesized in the same manner as synthesizing the title compound of Example 25 with using 5-bromo-N-(5-carbamoyl-2-adamantyl)-1-methylpyrrole-2-carboxamide (from Preparation Example 3) and 3-chlorophenyl boronic acid as a starting material (yield: 85%).

$^1$H-NMR (CDCl$_3$, 500 MHz) δ 7.35 (m, 3H), 6.62 (s, 1H), 6.22 (d, 1H), 6.19 (s, 1H), 5.62 (s, 1H), 5.46 (s, 1H), 4.19 (d, 1H), 3.87 (s, 3H), 2.19 (s, 2H), 2.04 (m, 5H), 1.93 (s, 2H), 1.88~1.67 (dd, 4H)

Example 34

Synthesis of N-(5-carbamoyl-2-adamantyl)-1-methyl-5-phenylpyrrole-2-carboxamide (A: VII, X: N—Y, Y: methyl group, R1: phenyl group)

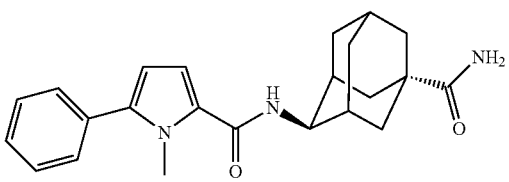 [SMILES: Cn1c(C(=O)N[C@H]2C3CC4CC2C[C@](C(N)=O)(C4)C3)ccc1-c1ccccc1]

The title compound was synthesized in the same manner as synthesizing the title compound of Example 25 with using 5-bromo-N-(5-carbamoyl-2-adamantyl)-1-methylpyrrole-2-carboxamide (from Preparation Example 3) and 3-chlorophenyl boronic acid as a starting material (yield: 90%).

¹H-NMR (CDCl₃, 500 MHz) δ 7.43 (m, 5H), 6.64 (d, 1H), 6.21 (d, 1H), 6.18 (s, 1H), 5.60 (s, 1H), 5.30 (s, 1H), 4.19 (d, 1H), 3.87 (s, 3H), 2.19 (s, 2H), 2.08 (m, 5H), 1.94 (s, 2H), 1.89~1.60 (dd, 4H)

Example 35

Synthesis of N-(5-carbamoyl-2-adamantyl)-5-(4-chlorophenyl)-1-methylpyrrole-2-carboxamide (A: VII, X: N—Y, Y: methyl group, R1: 4-chlorophenyl group)

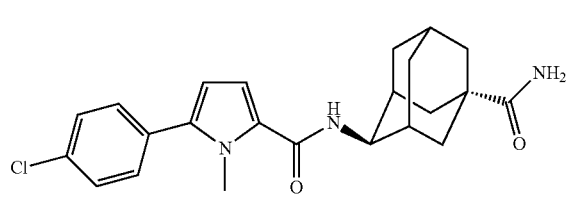 [SMILES: Cn1c(C(=O)N[C@H]2C3CC4CC2C[C@](C(N)=O)(C4)C3)ccc1-c1ccc(Cl)cc1]

The title compound was synthesized in the same manner as synthesizing the title compound of Example 25 with using 5-bromo-N-(5-carbamoyl-2-adamantyl)-1-methylpyrrole-2-carboxamide (from Preparation Example 3) and 4-chlorophenyl boronic acid as a starting material (yield: 85%).

¹H-NMR (CDCl₃, 500 MHz) δ 7.41 (d, 2H), 7.33 (d, 2H), 6.61 (d, 1H), 6.20 (d, 1H), 6.17 (s, 1H), 5.59 (s, 1H), 5.24 (s, 1H), 4.18 (d, 1H), 3.85 (s, 3H), 2.19 (s, 2H), 2.08 (m, 5H), 1.94 (s, 2H), 1.88~1.66 (dd, 4H)

Example 36

Synthesis of N-(5-carbamoyl-2-adamantyl)-5-(4-fluorophenyl)-1-methylpyrrole-2-carboxamide (A: VII, X: N—Y, Y: methyl group, R1: 4-fluorophenyl group)

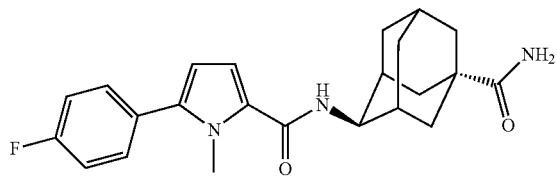 [SMILES: Cn1c(C(=O)N[C@H]2C3CC4CC2C[C@](C(N)=O)(C4)C3)ccc1-c1ccc(F)cc1]

The title compound was synthesized in the same manner as synthesizing the title compound of Example 25 with using 5-bromo-N-(5-carbamoyl-2-adamantyl)-1-methylpyrrole-2-carboxamide (from Preparation Example 3) and 4-fluorophenyl boronic acid as a starting material (yield: 87%).

¹H-NMR (CDCl₃, 500 MHz) δ 7.36 (m, 2H), 7.13 (m, 2H), 6.62 (s, 1H), 6.21 (d, 1H), 6.15 (s, 1H), 5.59 (s, 1H), 5.25 (s, 1H), 4.19 (d, 1H), 3.83 (s, 3H), 2.19 (s, 2H), 2.08 (m, 5H), 1.94 (s, 2H), 1.89~1.66 (dd, 4H)

Example 37

Synthesis of N-(5-carbamoyl-2-adamantyl)-1-methyl-5-[4-(trifluoromethyl)phenyl]pyrrole-2-carboxamide (A: VII, X: N—Y, Y: methyl group, R1: trifluorophenyl group)

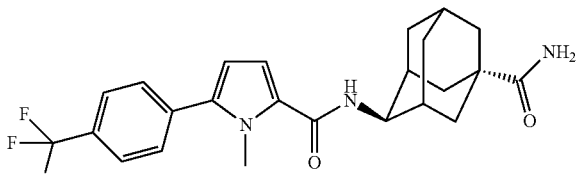

The title compound was synthesized in the same manner as synthesizing the title compound of Example 25 with using 5-bromo-N-(5-carbamoyl-2-adamantyl)-1-methylpyrrole-2-carboxamide (from Preparation Example 3) and 4-trifluorophenyl boronic acid as a starting material (yield: 80%).

¹H-NMR (CDCl₃, 500 MHz) δ 7.69 (d, 2H), 7.52 (d, 2H), 6.64 (s, 1H), 6.24 (s, 1H), 6.22 (d, 1H), 5.59 (s, 1H), 5.25 (s, 1H), 4.20 (d, 1H), 3.89 (s, 3H), 2.19 (s, 2H), 2.08 (m, 5H), 1.94 (s, 2H), 1.89~1.67 (dd, 4H)

Example 38

Synthesis of N-(5-carbamoyl-2-adamantyl)-5-(2-chlorophenyl)-1-methylpyrrole-2-carboxamide (A: VII, X: N—Y, Y: methyl group, R1: 2-chlorophenyl group)

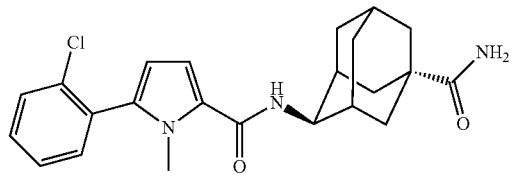 [SMILES: Cn1c(C(=O)N[C@H]2C3CC4CC2C[C@](C(N)=O)(C4)C3)ccc1-c1ccccc1Cl]

The title compound was synthesized in the same manner as synthesizing the title compound of Example 25 with using 5-bromo-N-(5-carbamoyl-2-adamantyl)-1-methylpyrrole-2-carboxamide (from Preparation Example 3) and 2-chlorophenyl boronic acid as a starting material (yield: 90%).

¹H-NMR (CDCl₃, 500 MHz) δ 7.48 (d, 1H), 7.35 (m, 3H), 6.65 (s, 1H), 6.23 (d, 1H), 6.17 (s, 1H), 5.61 (s, 1H), 5.51 (s,

1H), 4.18 (d, 1H), 3.72 (s, 3H), 2.19 (s, 2H), 2.08 (m, 5H), 1.94 (s, 2H), 1.90~1.66 (dd, 4H)

Example 39

Synthesis of N-(5-carbamoyl-2-adamantyl)-5-(2-fluorophenyl)-1-methylpyrrole-2-carboxamide (A: VII, X: N—Y, Y: methyl group, R1: 2-fluorophenyl group)

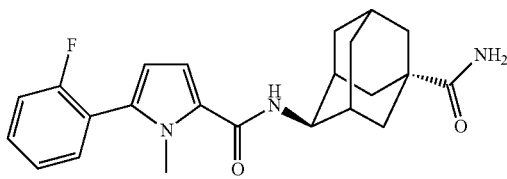 [SMILES: Cn1c(C(=O)N[C@H]2C3CC4CC2C[C@](C(N)=O)(C4)C3)ccc1-c1ccccc1F]

The title compound was synthesized in the same manner as synthesizing the title compound of Example 25 with using 5-bromo-N-(5-carbamoyl-2-adamantyl)-1-methylpyrrole-2-carboxamide (from Preparation Example 3) and 2-fluorophenyl boronic acid as a starting material (yield: 87%).

$^1$H-NMR (CDCl$_3$, 500 MHz) δ 7.38 (m, 1H), 7.33 (m, 1H), 7.22 (m, 1H), 7.16 (m, 1H), 6.65 (s, 1H), 6.22 (d, 1H), 6.20 (s, 1H), 5.59 (s, 1H), 5.26 (s, 1H), 4.19 (d, 1H), 3.79 (s, 3H), 2.19 (s, 2H), 2.08 (m, 5H), 1.94 (s, 2H), 1.89~1.66 (dd, 4H)

Example 40

Synthesis of N-(5-carbamoyl-2-adamantyl)-5-phenylthiophene-2-carboxamide (A: VII, X: S, R1: phenyl group)

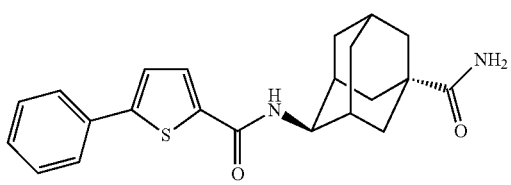

The title compound was synthesized in the same manner as synthesizing the title compound of Example 25 with using 5-bromo-N-(5-carbamoyl-2-adamantyl)thiophene-2-carboxamide (Preparation Example 4) and phenyl boronic acid as a starting material (yield: 90%).

$^1$H-NMR (CDCl$_3$, 500 MHz) δ 7.64 (d, 2H), 7.41 (m, 2H), 7.35 (d, 1H), 7.27 (d, 1H), 6.19 (d, 1H), 5.58 (s, 1H), 5.21 (s, 1H), 4.23 (d, 1H), 2.22 (s, 2H), 2.09 (m, 5H), 1.95 (s, 2H), 1.89~1.68 (dd, 4H)

Example 41

Synthesis of N-(5-carbamoyl-2-adamantyl)-5-(4-chlorophenyl)thiophene-2-carboxamide (A: VII, X: S, R1: 4-chlorophenyl group)

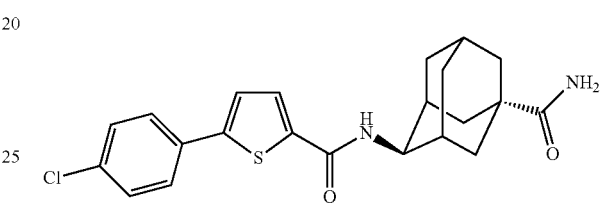

The title compound was synthesized in the same manner as synthesizing the title compound of Example 25 with using 5-bromo-N-(5-carbamoyl-2-adamantyl)thiophene-2-carboxamide (Preparation Example 4) and 4-chlorophenyl boronic acid as a starting material (yield: 90%).

$^1$H-NMR (CDCl$_3$, 500 MHz) δ 7.55 (d, 2H), 7.48 (s, 1H), 7.38 (d, 2H), 7.25 (d, 1H), 6.18 (d, 1H), 5.58 (s, 1H), 5.20 (s, 1H), 4.23 (d, 1H), 2.22 (s, 2H), 2.08 (m, 5H), 1.95 (s, 2H), 1.88~1.68 (dd, 4H)

Example 42

Synthesis of N-(5-carbamoyl-2-adamantyl)-5-(3-chlorophenyl)thiophene-2-carboxamide (A: VII, X: S, R1: 3-chlorophenyl group)

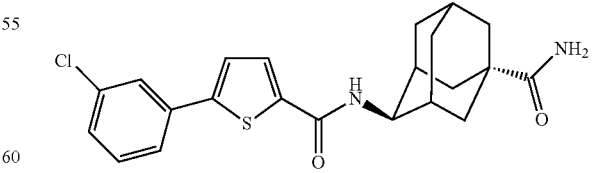

The title compound was synthesized in the same manner as synthesizing the title compound of Example 25 with using 5-bromo-N-(5-carbamoyl-2-adamantyl)thiophene-2-carboxamide (Preparation Example 4) and 3-chlorophenyl boronic acid as a starting material (yield: 85%).

¹H-NMR (CDCl₃, 500 MHz) δ 7.61 (s, 1H), 7.49 (m, 2H), 7.34 (m, 2H), 7.27 (d, 1H), 6.20 (d, 1H), 5.59 (s, 1H), 5.24 (s, 1H), 4.23 (d, 1H), 2.22 (s, 2H), 2.09 (m, 5H), 1.94 (s, 2H), 1.88~1.68 (dd, 4H)

Example 43

Synthesis of N-(5-carbamoyl-2-adamantyl)-5-(2-chlorophenyl)thiophene-2-carboxamide (A: VII, X: S, R1: 2-chlorophenyl group)

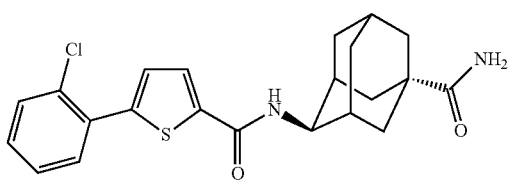

The title compound was synthesized in the same manner as synthesizing the title compound of Example 25 with using 5-bromo-N-(5-carbamoyl-2-adamantyl)thiophene-2-carboxamide (Preparation Example 4) and 2-chlorophenyl boronic acid as a starting material (yield: 87%).

¹H-NMR (CDCl₃, 500 MHz) δ 7.53 (m, 2H), 7.32 (m, 2H), 6.22 (d, 1H), 5.59 (s, 1H), 5.22 (s, 1H), 4.23 (d, 1H), 2.22 (s, 2H), 2.08 (m, 5H), 1.94 (s, 2H), 1.88~1.67 (dd, 4H)

Example 44

Synthesis of N-(5-carbamoyl-2-adamantyl)-5-(2-fluorophenyl)thiophene-2-carboxamide (A: VII, X: S, R1: 2-fluorophenyl group)

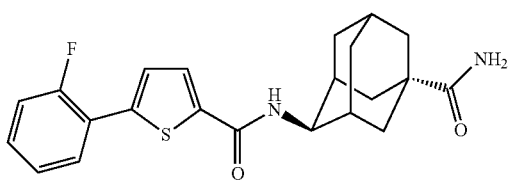

The title compound was synthesized in the same manner as synthesizing the title compound of Example 25 with using 5-bromo-N-(5-carbamoyl-2-adamantyl)thiophene-2-carboxamide (Preparation Example 4) and 2-fluorophenyl boronic acid as a starting material (yield: 85%).

¹H-NMR (CDCl₃, 500 MHz) δ 7.65 (t, 1H), 7.52 (s, 1H), 7.43 (s, 1H), 7.31 (m, 1H), 7.18 (m, 2H), 6.21 (d, 1H), 5.62 (s, 1H), 5.31 (s, 1H), 4.23 (d, 1H), 2.22 (s, 2H), 2.08 (m, 5H), 1.94 (s, 2H), 1.89~1.67 (dd, 4H)

Example 45

Synthesis of N-(5-carbamoyl-2-adamantyl)-6-methoxypyridine-2-carboxamide (A: II, R1: methoxy group)

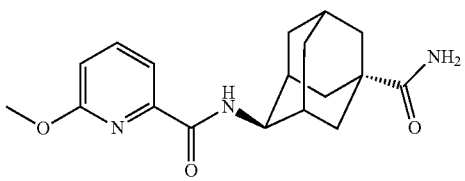 [SMILES: COc1cccc(C(=O)N[C@H]2C3CC4CC2C[C@](C(N)=O)(C4)C3)n1]

N-(5-carbamoyl-2-adamantyl)-6-hydroxypyridine-2-carboxamide was synthesized in the same manner as synthesizing the title compound of Preparation Example 2 with using 6-hydroxy pyridine-2-carboxylic acid as a starting material.

100 mg of N-(5-carbamoyl-2-adamantyl)-6-hydroxypyridine-2-carboxamide was dissolved in DMF and then 67 mg of methyl iodide and 87 mg of K₂CO₃ were added thereto and stirred for 12 hours. After DMF was dried off under a reduced pressure, ethyl acetate and water were added to the resulting product to make a layer separation. The organic layer was collected and dried over MgSO₄ and then filtered and distilled under a reduced pressure.

The resulting produce was purified by using a tube chromatography (MC:MeOH=19:1, (v/v)) to produce 78 mg of a white solid product.

¹H-NMR (CDCl₃, 500 MHz) δ 8.36 (d, 1H), 7.80 (s, 1H), 7.73 (s, 1H), 6.91 (d, 1H), 5.58 (s, 1H), 5.18 (s, 1H), 4.24 (d, 1H), 3.99 (s, 3H), 2.21 (s, 2H), 2.17 (s, 1H), 2.08 (m, 4H), 1.95 (s, 2H), 1.93~1.54 (dd, 4H)

Example 46

Synthesis of N-(5-carbamoyl-2-adamantyl)-6-propoxypyridine-2-carboxamide (A: II, R1: propoxy group)

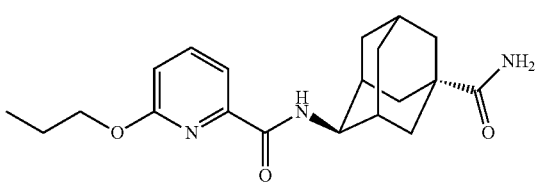 [SMILES: CCCOc1cccc(C(=O)N[C@H]2C3CC4CC2C[C@](C(N)=O)(C4)C3)n1]

The title compound was synthesized in the same manner as synthesizing the title compound of Example 45 with using N-(5-carbamoyl-2-adamantyl)-6-hydroxypyridine-2-carboxamide (an intermediate of Example 45) and propyl iodide as a starting material (yield: 80%).

¹H-NMR (CDCl₃, 500 MHz) δ 8.35 (d, 1H), 7.77 (d, 1H), 7.71 (t, 1H), 6.88 (d, 1H), 5.59 (s, 1H), 5.21 (s, 1H), 4.30 (t,

2H), 4.23 (d, 1H), 2.20 (s, 2H), 2.17 (s, 1H), 2.06 (m, 4H), 1.95 (s, 2H), 1.86 (m, 4H), 1.69 (d, 2H), 1.05 (3, 3H)

Example 47

Synthesis of N-(5-carbamoyl-2-adamantyl)-6-phenylmethoxypyridine-2-carboxamide (A: II, R1: phenylmethoxy group)

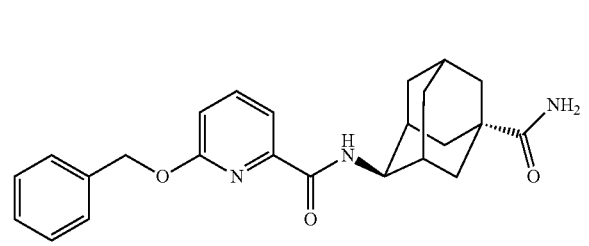 [SMILES: NC(=O)[C@]12CC3CC(C1)[C@@H](NC(=O)c1cccc(OCc4ccccc4)n1)C(C3)C2]

The title compound was synthesized in the same manner as synthesizing the title compound of Example 45 with using N-(5-carbamoyl-2-adamantyl)-6-hydroxypyridine-2-carboxamide (an intermediate of Example 45) and benzyl bromide as a starting material (yield: 78%).

$^1$H-NMR (CDCl$_3$, 500 MHz) δ 8.20 (d, 1H), 7.81 (d, 1H), 7.75 (t, 1H), 7.43~7.30 (m, 5H), 6.98 (d, 1H), 5.58 (s, 1H), 5.44 (s, 2H), 5.21 (s, 1H), 4.21 (d, 1H), 2.17 (s, 2H), 2.05 (m, 5H), 1.94 (s, 2H), 1.80~1.62 (dd, 4H)

Example 48

Synthesis of N-(5-carbamoyl-2-adamantyl)-6-[(3,5-dimethyl-1,2-oxazol-4-yl)methoxy]pyridine-2-carboxamide (A: II, R1: dimethyl oxazolyl methoxy group)

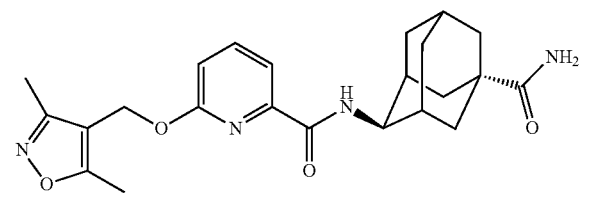 [SMILES: Cc1noc(C)c1COc1cccc(C(=O)N[C@H]2C3CC4CC2C[C@](C(N)=O)(C4)C3)n1]

The title compound was synthesized in the same manner as synthesizing the title compound of Example 45 with using N-(5-carbamoyl-2-adamantyl)-6-hydroxypyridine-2-carboxamide (an intermediate of Example 45) and 4-chloromethyl-3,5-dimethyl-isoxazole as a starting material (yield: 75%).

$^1$H-NMR (CDCl$_3$, 500 MHz) δ 8.20 (d, 1H), 7.86 (d, 1H), 7.77 (t, 1H), 6.90 (d, 1H), 5.58 (s, 1H), 5.20 (s, 1H), 5.16 (s, 2H), 4.26 (d, 1H), 2.44 (s, 3H), 2.31 (s, 3H), 2.23 (s, 2H), 2.08 (m, 5H), 1.96 (s, 2H), 1.92~1.70 (dd, 4H)

Example 49

Synthesis of N-(5-carbamoyl-2-adamantyl)-8-propoxyquinoline-2-carboxamide (A: III, R1: propoxy group)

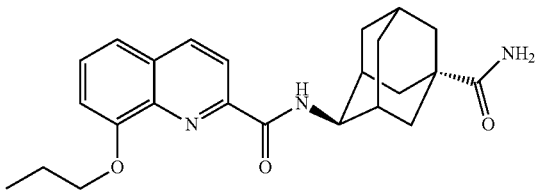 [SMILES: CCCOc1cccc2ccc(C(=O)N[C@H]3C4CC5CC3C[C@](C(N)=O)(C5)C4)nc12]

100 mg of N-(5-carbamoyl-2-adamantyl)-8-hydroxyquinoline-2-carboxamide (Example 20) was dissolved in DMF, and 70 mg of propyl iodide and 76 mg of K$_2$CO$_3$ were added thereto and stirred for 12 hours. After DMF was dried off under a reduced pressure therefrom, ethyl acetate and water were added to the reaction product to make a layer separation. The organic layer was collected and dried over MgSO$_4$ and then filtered and distilled under a reduced pressure. The compound thus obtained was purified via a tube chromatography (MC:MeOH=19:1, (v/v)) to produce 70 mg of a white solid product.

$^1$H-NMR (CDCl$_3$, 500 MHz) δ 9.04 (d, 1H), 8.29 (q, 2H), 7.52 (t, 1H), 7.43 (d, 1H), 7.08 (d, 1H), 5.62 (s, 1H), 5.26 (s, 1H), 4.30 (d, 1H), 4.17 (t, 2H), 2.25 (s, 2H), 2.09 (m, 9H), 1.97 (m, 2H), 1.70 (d, 2H), 1.21 (t, 3H)

Example 50

Synthesis of N-(5-carbamoyl-2-adamantyl)-8-methoxyquinoline-2-carboxamide (A: III, R1: methoxy group)

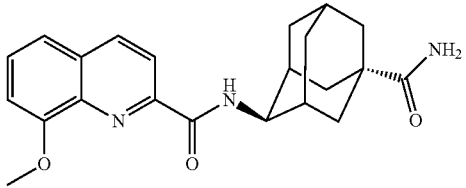 [SMILES: COc1cccc2ccc(C(=O)N[C@H]3C4CC5CC3C[C@](C(N)=O)(C5)C4)nc12]

The title compound was synthesized in the same manner as synthesizing the title compound of Example 49 with using N-(5-carbamoyl-2-adamantyl)-8-hydroxyquinoline-2-carboxamide (Example 20) and methyl iodide as a starting material (yield: 85%).

¹H-NMR (CDCl₃, 500 MHz) δ 8.78 (d, 1H), 8.30 (q, 2H), 7.54 (t, 1H), 7.45 (d, 1H), 7.10 (d, 1H), 5.64 (s, 1H), 5.34 (s, 1H), 4.28 (d, 1H), 4.10 (s, 3H), 2.30 (s, 2H), 2.10 (m, 7H), 1.97 (s, 2H), 1.70 (d, 2H)

Example 51

Synthesis of N-(5-carbamoyl-2-adamantyl)-8-ethoxyquinoline-2-carboxamide (A: III, R1: ethoxy group)

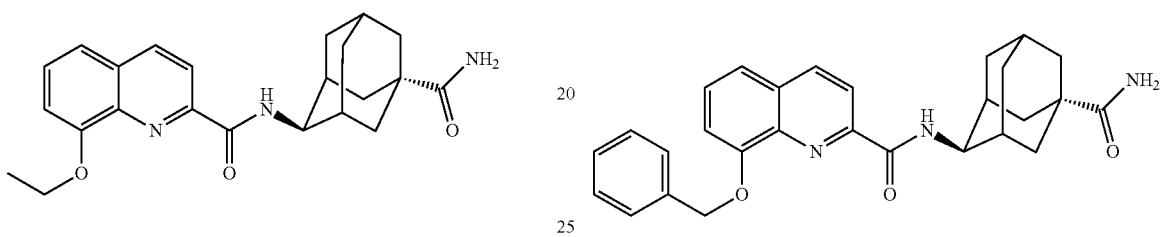

The title compound was synthesized in the same manner as synthesizing the title compound of Example 49 with using N-(5-carbamoyl-2-adamantyl)-8-hydroxyquinoline-2-carboxamide (Example 20) and ethyl iodide as a starting material (yield: 85%).

¹H-NMR (CDCl₃, 500 MHz) δ 9.03 (d, 1H), 8.29 (s, 2H), 7.52 (t, 1H), 7.44 (d, 1H), 7.08 (d, 1H), 5.65 (s, 1H), 5.43 (s, 1H), 4.28 (m, 3H), 2.26 (s, 2H), 2.10 (m, 7H), 1.97 (s, 2H), 1.72 (d, 2H), 1.62 (t, 3H)

Example 52

Synthesis of N-(5-carbamoyl-2-adamantyl)-8-propan-2-yloxyquinoline-2-carboxamide (A: III, R1: 1-methylethoxy group)

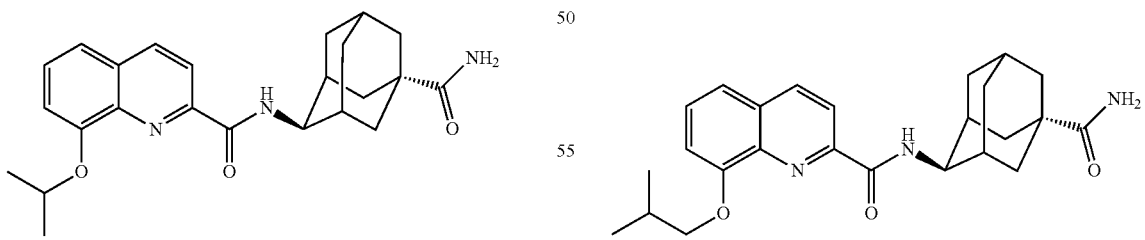

The title compound was synthesized in the same manner as synthesizing the title compound of Example 49 with using N-(5-carbamoyl-2-adamantyl)-8-hydroxyquinoline-2-carboxamide (Example 20) and 2-bromopropane as a starting material (yield: 80%).

¹H-NMR (CDCl₃, 500 MHz) δ 9.04 (d, 1H), 8.27 (s, 2H), 7.52 (t, 1H), 7.45 (d, 1H), 7.15 (d, 1H), 5.65 (s, 1H), 5.38 (s, 1H), 4.85 (m, 1H), 4.29 (d, 1H), 2.26 (s, 2H), 2.13 (m, 7H), 1.97 (s, 2H), 1.72 (d, 2H), 1.50 (d, 6H)

Example 53

Synthesis of N-(5-carbamoyl-2-adamantyl)-8-benzylmethoxyquinoline-2-carboxamide (A: III, R1: benzyl methoxy group)

The title compound was synthesized in the same manner as synthesizing the title compound of Example 49 with using N-(5-carbamoyl-2-adamantyl)-8-hydroxyquinoline-2-carboxamide (Example 20) and benzyl bromide as a starting material (yield: 85%).

¹H-NMR (CDCl₃, 500 MHz) δ 8.90 (d, 1H), 8.31 (q, 2H), 7.62 (m, 2H), 7.55 (t, 1H), 7.49 (d, 1H), 7.40 (m, 3H), 7.20 (d, 1H), 5.65 (s, 1H), 5.45 (s, 1H), 5.30 (s, 3H), 4.28 (d, 1H), 2.20 (s, 2H), 2.07 (m, 5H), 1.94 (s, 2H), 1.91~1.57 (dd, 4H)

Example 54

Synthesis of N-(5-carbamoyl-2-adamantyl)-8-(2-methylpropoxy)quinoline-2-carboxamide (A: III, R1: 2-methylpropoxy group)

The title compound was synthesized in the same manner as synthesizing the title compound of Example 49 with using N-(5-carbamoyl-2-adamantyl)-8-hydroxyquinoline-2-carboxamide (Example 20) and 1-bromo-2-methylpropane as a starting material (yield: 85%).

¹H-NMR (CDCl₃, 500 MHz) δ 9.03 (d, 1H), 8.27 (q, 2H), 7.49 (t, 1H), 7.41 (d, 1H), 7.05 (d, 1H), 5.60 (s, 1H), 5.23 (s,

1H), 4.30 (d, 1H), 3.96 (d, 2H), 2.29 (m, 1H), 2.22 (s, 2H), 2.08 (m, 7H), 1.95 (s, 2H), 1.69 (d, 2H), 1.17 (d, 6H)

Example 55

Synthesis of N-(5-carbamoyl-2-adamantyl)-8-(cyclohexylmethoxy)quinoline-2-carboxamide (A: III, R1: cyclohexyl methoxy group)

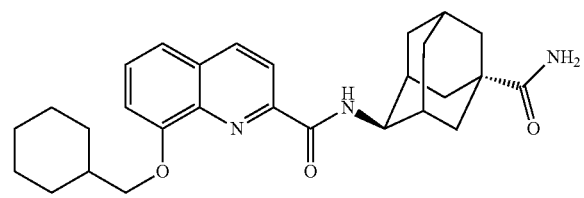 [SMILES: NC(=O)[C@]12CC3CC(C1)[C@@H](NC(=O)c1ccc4cccc(OCC5CCCCC5)c4n1)C(C3)C2]

The title compound was synthesized in the same manner as synthesizing the title compound of Example 49 with using N-(5-carbamoyl-2-adamantyl)-8-hydroxyquinoline-2-carboxamide (Example 20) and cyclohexyl bromide as a starting material (yield: 87%).

$^1$H-NMR (CDCl$_3$, 500 MHz) δ 8.97 (d, 1H), 8.29 (q, 2H), 7.51 (t, 1H), 7.42 (d, 1H), 7.07 (d, 1H), 5.63 (s, 1H), 5.30 (s, 1H), 4.33 (d, 1H), 3.99 (d, 2H), 2.25 (s, 2H), 2.10 (m, 11H), 1.97 (s, 2H), 1.83 (d, 2H), 1.73 (m, 4H), 1.35 (m, 2H), 1.24 (m, 4H)

Example 56

Synthesis of 8-butan-2-yloxy-N-(5-carbamoyl-2-adamantyl)quinoline-2-carboxamide (A: III, R1: 1-methylpropoxy group)

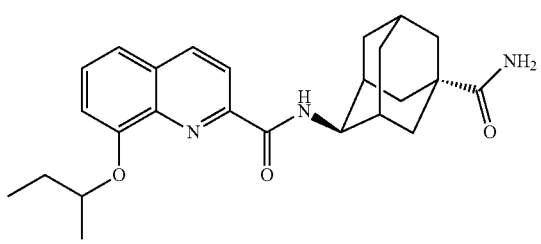 [SMILES: CCC(C)Oc1cccc2ccc(C(=O)N[C@H]3C4CC5CC3C[C@](C(N)=O)(C5)C4)nc12]

The title compound was synthesized in the same manner as synthesizing the title compound of Example 49 with using N-(5-carbamoyl-2-adamantyl)-8-hydroxyquinoline-2-carboxamide (Example 20) and 2-bromobutane as a starting material (yield: 85%).

$^1$H-NMR (CDCl$_3$, 500 MHz) δ 9.07 (d, 1H), 8.30 (s, 2H), 7.54 (t, 1H), 7.46 (d, 1H), 7.14 (d, 1H), 5.65 (s, 1H), 5.31 (s, 1H), 4.64 (q, 1H), 4.33 (d, 1H), 2.27 (s, 2H), 0.2.09 (m, 7H), 1.99 (s, 2H), 1.94 (m, 1H), 1.86 (m, 1H), 1.76 (m, 2H), 1.49 (d, 3H), 1.12 (t, 3H)

Example 57

Synthesis of N-(5-carbamoyl-2-adamantyl)-6-(dimethylamino)pyridine-2-carboxamide (A: II, R1: dimethyl amino group)

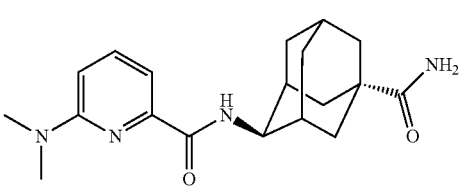 [SMILES: CN(C)c1cccc(C(=O)N[C@H]2C3CC4CC2C[C@](C(N)=O)(C4)C3)n1]

100 mg of N-(5-carbamoyl-2-adamantyl)-6-chloropyridine-2-carboxamide (from Preparation Example 5) was dissolved in DMSO, and 34 mg of dimethylamine was added thereto, and the resulting mixture reacted in a microwave reactor at 75° C. for 10 minutes. 10 mL of ethyl acetate was added to the reaction product, which was then washed with water and brine. The resulting organic solution was dried over MgSO$_4$ and then filtered and distilled under a reduced pressure. The product thus obtained was purified with prep LC to produce 50 mg of the title compound.

$^1$H-NMR (CDCl$_3$, 500 MHz) δ 8.56 (m, 1H), 7.59 (m, 1H), 7.45 (d, 1H), 6.68 (d, 1H), 5.61 (br, 1H), 5.26 (br, 1H), 4.22 (m, 1H), 3.13 (s, 6H), 2.19~1.92 (m, 11H), 1.67 (d, 2H)

Example 58

Synthesis of N-(5-carbamoyl-2-adamantyl)-6-piperidin-1-yl-pyridine-2-carboxamide (A: II, R1: piperidine group)

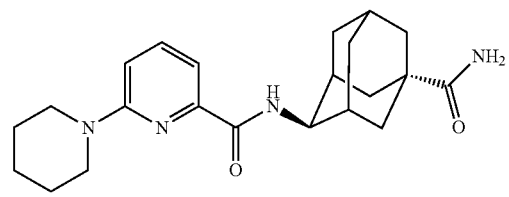 [SMILES: NC(=O)[C@]12CC3CC(C1)[C@@H](NC(=O)c1cccc(N4CCCCC4)n1)C(C3)C2]

The title compound was synthesized in the same manner as synthesizing the title compound of Example 57 with using N-(5-carbamoyl-2-adamantyl)-6-chloropyridine-2-carboxamide (Preparation Example 5) and piperidine as a starting material (yield: 80%).

¹H-NMR (CDCl3, 500 MHz) δ 8.50 (d, 1H), 7.62 (t, 1H), 7.49 (d, 1H), 6.84 (d, 1H), 5.62 (br, 1H), 5.23 (br, 1H), 4.23 (m, 1H), 3.60 (m, 4H), 2.22~1.91 (m, 11H), 1.67 (d, 2H), 0.89 (m, 6H)

Example 59

Synthesis of N-(5-carbamoyl-2-adamantyl)-6-(diethylamino)pyridine-2-carboxamide (A: II, R1: diethylamino group)

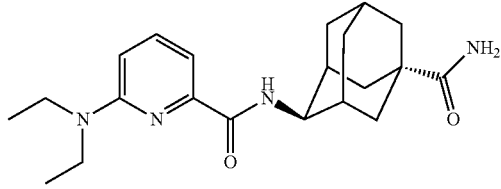 [SMILES: CCN(CC)c1cccc(C(=O)N[C@H]2C3CC4CC2C[C@](C(N)=O)(C4)C3)n1]

The title compound was synthesized in the same manner as synthesizing the title compound of Example 57 with using N-(5-carbamoyl-2-adamantyl)-6-chloropyridine-2-carboxamide (Preparation Example 5) and diethylamine as a starting material (yield: 80%).

¹H-NMR (CDCl3, 500 MHz) δ 8.60 (d, 1H), 7.56 (t, 1H), 7.39 (d, 1H), 6.62 (d, 1H), 5.62 (br, 1H), 5.28 (br, 1H), 4.21 (m, 1H), 3.53 (m, 4H), 2.17=1.91 (m, 11H), 1.67 (d, 2H), 1.22 (t, 6H)

Example 60

Synthesis of N-(5-carbamoyl-2-adamantyl)-6-(propylamino)pyridine-2-carboxamide (A: II, R1: propylamino group)

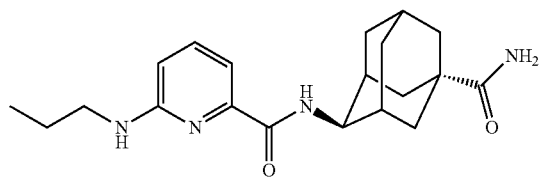 [SMILES: CCCNc1cccc(C(=O)N[C@H]2C3CC4CC2C[C@](C(N)=O)(C4)C3)n1]

The title compound was synthesized in the same manner as synthesizing the title compound of Example 57 with using N-(5-carbamoyl-2-adamantyl)-6-chloropyridine-2-carboxamide (Preparation Example 5) and propylamine as a starting material (yield: 50%).

¹H-NMR (CDCl3, 500 MHz) δ 8.50 (d, 1H), 7.57 (t, 1H), 7.48 (d, 1H), 6.54 (d, 1H), 5.66 (br, 1H), 5.42 (br, 1H), 4.64 (br, 1H), 4.24 (m, 1H), 3.33 (m, 2H), 2.24~1.94 (m, 11H), 1.71 (d, 4H), 1.04 (t, 3H)

Example 61

Synthesis of N-(5-carbamoyl-2-adamantyl)6-(3,4-dihydro-1H-isoquinolin-2-yl)pyridine-2-carboxamide (A: II, R1: 3,4-dihydro-1H-isoquinoline group)

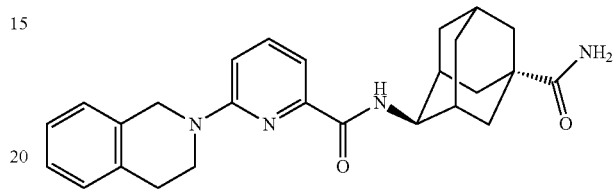

The title compound was synthesized in the same manner as synthesizing the title compound of Example 57 with using N-(5-carbamoyl-2-adamantyl)-6-chloropyridine-2-carboxamide (Preparation Example 5) and 1,2,3,4-tetrahydro-isoquinoline as a starting material (yield: 83%).

¹H-NMR (CDCl3, 500 MHz) δ 8.55 (d, 1H), 7.65 (t, 1H), 7.51 (d, 1H). 7.23~7.17 (m, 4H), 6.86 (d, 1H), 5.63 (br, 1H), 5.29 (br, 1H), 4.76 (s, 2H), 4.23 (m, 1H), 3.88 (t, 2H), 3.01 (t, 2H), 2.21~1.97 (m, 11H), 1.72 (m, 2H)

Example 62

Synthesis of N-(5-carbamoyl-2-adamantyl)-6-(4-phenylpiperidin-1-yl)pyridine-2-carboxamide (A: II, R1: phenyl piperidine group)

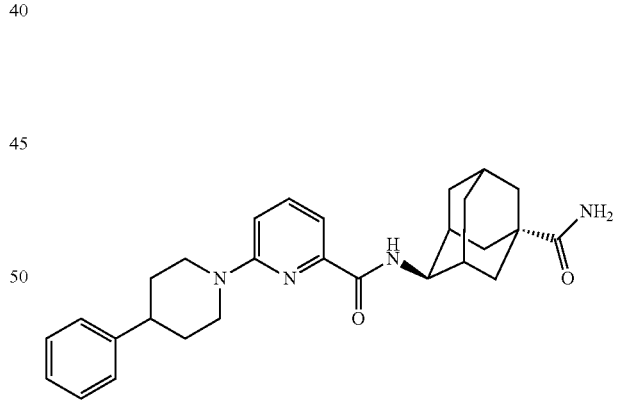

The title compound was synthesized in the same manner as synthesizing the title compound of Example 57 with using N-(5-carbamoyl-2-adamantyl)-6-chloropyridine-2-carboxamide (Preparation Example 5) and 4-phenylpiperidine as a starting material (yield: 85%).

¹H-NMR (CDCl3, 500 MHz) δ 8.46 (d, 1H), 7.63 (t, 1H), 7.50 (d, 1H), 7.33~7.22 (m, 5H), 6.88 (d, 1H), 5.66 (br, 1H), 5.44 (br, 1H), 4.44 (d, 2H), 4.20 (d, 1H), 3.48 (s, 2H), 3.02 (t, 2H), 2.79 (t, 1H), 2.18 (s, 2H), 2.05~1.64 (m, 13H)

Example 63

N-(5-carbamoyl-2-adamantyl)-6-methyl-1-oxidopyridine-1-ium-2-carboxamide (A: V, R1: methyl group)

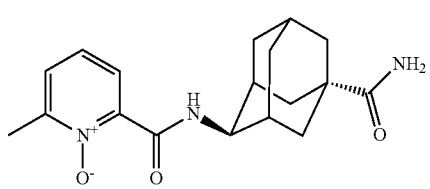 [SMILES: Cc1cccc(C(=O)N[C@H]2C3CC4CC2C[C@](C(N)=O)(C4)C3)[n+]1[O-]]

50 mg of N-(5-carbamoyl-2-adamantyl)-6-methylpyridine-2-carboxamide (Example 15) was dissolved in methanol and then 200 mg of magnesium bismonoperoxy phthalate hexahydrate (MMPP) was added thereto and stirred at 65° C. for 3 hours. After the addition of ethyl acetate, the reaction product was filtered by using Celite. The organic layer was washed with water, dried over $MgSO_4$, and then filtered and distilled under a reduced pressure. The produce thus obtained was purified with using a tube chromatography (MC:MeOH=19:1, (v/v)) to produce 34 mg of a white solid product.

$^1$H-NMR ($CDCl_3$, 500 MHz) δ 12.05 (d, 1H), 8.36 (d, 1H), 7.39 (m, 1H), 5.59 (s, 1H), 5.24 (s, 1H), 4.31 (d, 1H), 2.56 (s, 3H), 2.20 (s, 2H), 2.08 (m, 7H), 1.94 (s, 2H), 1.65 (d, 2H)

Example 64

Synthesis of N-(5-carbamoyl-2-adamantyl)-1-oxidoquinolin-1-ium-2-carboxamide (A: VI, R1: H)

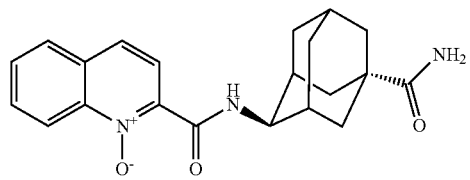 [SMILES: NC(=O)[C@]12CC3CC(C1)[C@@H](NC(=O)c1ccc4ccccc4[n+]1[O-])C(C3)C2]

The title compound was synthesized in the same manner as synthesizing the title compound of Example 63 with using N-(5-carbamoyl-2-adamantyl)quinoline-2-carboxamide (Example 18) as a starting material (yield: 65%).

$^1$H-NMR ($CDCl_3$, 500 MHz) δ 12.15 (d, 1H), 8.83 (d, 1H), 8.45 (d, 1H), 7.85 (m, 3H), 7.73 (m, 1H), 5.60 (s, 1H), 5.23 (s, 1H), 4.37 (d, 1H), 2.26 (s, 2H), 2.09 (m, 7H), 1.97 (s, 2H), 1.69 (d, 2H)

Example 65

Synthesis of N-(5-carbamoyl-2-adamantyl)-6-(dimethylamino)-1-oxidopyridin-1-ium-2-carboxamide (A: V, R1: dimethylamino group)

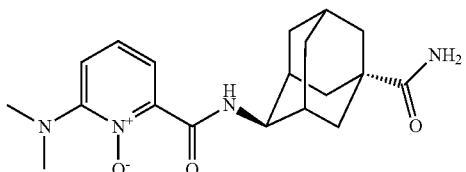

27 mg of N-(5-carbamoyl-2-adamantyl)-6-(dimethylamino)pyridine-2-carboxamide (Example 57) was dissolved in methanol, and then 150 mg of magnesium bismonoperoxy phthalate hexahydrate (MMPP) was added thereto and stirred at 65° C. for 3 hours. The solids in the reactor was filtered off and washed with methanol in PolarPak Rxn CX. From the resulting product, a desired product was dissolved out with using $NH_3$ (7N in MeOH) and the resulting solution was distilled under a reduced pressure. The substance thus obtained was purified with using a tube chromatography (MC:MeOH=19:1 (v/v)) to produce 15 mg of a white solid product.

$^1$H-NMR ($CDCl_3$, 500 MHz) δ 8.84 (d, 1H), 8.30 (d, 1H), 8.16 (t, 1H), 7.96 (d, 1H), 6.15 (d, 1H), 5.60 (s, 1H), 5.27 (s, 1H), 4.27 (d, 1H), 3.65 (s, 6H), 2.22 (s, 2H), 2.09 (m, 5H), 1.97 (s, 2H), 1.85~1.72 (dd, 4H)

Experimental Examples

Tests for Pharmacological Activity

With the compound of Chemical Formula I and pharmaceutically acceptable acid salt thereof; the activity of inhibiting 11β-HSD1 was tested in the following manners:
(1) Source of Enzyme
cDNA (human: Accession No. U12978.2; mouse: Accession No. NM_008288.2) coding the full-length amino acid sequence of 11β-HSD1 in a human and a mouse was incorporated into pMSCVpuro (from Clontech. Co. Ltd.), a vector of expressing a mammalian cell for the production of a retrovirus, and the resulting product was introduced into a GP2-293 cell (from Clontech Co. Ltd.), a retrovirus packing cell line together with pVSV-G vector (from Clontech Co. Ltd.) by using a Lipotamine plus reagent (from Invitrogen Co. Ltd.) in accordance with the method set forth in the appendix (by using HTRF cortisol assay kit from Cisbio assays Co., Ltd., catalog No. 62CO2PEB) and stabilized for 48 hours. Thereafter, viruses being obtained from those cells were used to infect CHO-K1 cell (from Korean Cell Line Bank, KCLB No. 10061) and in 24 hours, the cells were treated with 10 μg/ml pumycin (from Sigma Co. Ltd.) for two weeks to produce a stabilized cell system wherein each 11β-HSD1 in humans or in mice was over-expressed. When the cells being maintained, 5 μg/ml of puromycin was put into the medium and used (RPMI (Gibco), 37° C.).

Reference material: The EMBO Journal (2008) 27, 642-653

(2) Measurement of Inhibition Constant of the Enzyme

The obtained cells with 11b-HSD1 in a human and a mouse being over-expressed were sub-cultured in a 96-well plate with a cell number being $3\times10^4$ cells per well and stabilized for 24 hours [RPMI (Gibco), at 37° C., as being used in 5 days after thawing]. After a medium as diluted with DMSO including 160 nM of cortisone (from Sigma Co. Ltd.) and a test compound at a different concentration was put into each well in an amount of 200 ul, the well was cultured in a cell cultivator at 37° C. for 3 hours. 10 ul of the cultured solution was put into a 384 well plate and the amount of cortisol as generated was measured using a cortisol kit (from Cisbio international Co. Ltd, HTRF assay) in accordance with the method set forth in the appended manual.

As a control group, 160 nM of cortisone and 1% of DMSO were put into a corresponding well. The ground value was obtained from a well including only 160 nM of cortisone and 1% of DMSO without cells just like the control group. The calculation for a % inhibition level was made following the manual as appended.

Reference material: The Journal of Steroid Biochemistry and Molecular Biology, Volume 104, Issues 3-5, May 2007, Pages 123-129

Bioorganic & Medicinal Chemistry Letters Volume 19, Issue 10, 15 May 2009, Pages 2674-2678

Like the analyzing method as stated above, the efficacy of inhibiting 11b-HSD1 was calculated as $IC_{50}$ and the results are shown in Table 1:

TABLE 1

The inhibition constant of 11b HSD1 enzyme in humans and mice

| compound | Human 11b-HSD1 $IC_{50}$ (nM) | Mouse 11b-HSD1 $IC_{50}$ (nM) |
| --- | --- | --- |
| Example 1 | +++ | +++ |
| Example 2 | +++ | ++ |
| Example 3 | +++ | + |
| Example 4 | +++ | ++ |
| Example 6 | + | + |
| Example 7 | + | + |
| Example 8 | ++ | + |
| Example 12 | + | + |
| Example 13 | ++ | + |
| Example 15 | +++ | ++ |
| Example 16 | + | + |
| Example 17 | + | + |
| Example 18 | +++ | +++ |
| Example 19 | +++ | +++ |
| Example 21 | +++ | +++ |
| Example 22 | ++ | + |
| Example 23 | ++ | ++ |
| Example 24 | +++ | ++ |
| Example 25 | +++ | +++ |
| Example 26 | +++ | +++ |
| Example 27 | +++ | +++ |
| Example 28 | +++ | ++ |
| Example 29 | +++ | ++ |
| Example 30 | +++ | +++ |
| Example 31 | +++ | ++ |
| Example 32 | +++ | ++ |
| Example 33 | +++ | +++ |
| Example 34 | +++ | +++ |
| Example 35 | +++ | ++ |
| Example 36 | +++ | +++ |
| Example 37 | +++ | ++ |
| Example 38 | +++ | +++ |
| Example 39 | +++ | +++ |
| Example 40 | +++ | +++ |
| Example 41 | +++ | ++ |
| Example 42 | +++ | +++ |
| Example 43 | +++ | +++ |
| Example 44 | +++ | +++ |
| Example 45 | +++ | ++ |
| Example 46 | +++ | +++ |
| Example 47 | +++ | ++ |
| Example 48 | +++ | ND |
| Example 49 | +++ | ++ |
| Example 50 | +++ | ++ |
| Example 51 | +++ | +++ |
| Example 52 | +++ | ++ |
| Example 53 | +++ | + |
| Example 54 | +++ | + |
| Example 56 | +++ | ++ |
| Example 57 | +++ | +++ |
| Example 58 | +++ | +++ |
| Example 59 | +++ | +++ |
| Example 60 | +++ | +++ |
| Example 61 | +++ | +++ |
| Example 62 | +++ | ++ |
| Example 63 | ++ | + |
| Example 64 | + | ++ |
| Example 65 | +++ | ++ |

+++: IC50 < 100 nM,
++: 100 nM < IC50 < 500 nM,
+: 500 nM < IC50)

3) Ex Vivo Pd Assay

The prepared compound was orally administered to a mouse (C57B1/6, orient 8 week old, about 25 g, male) and in a proper amount of time (2 hours, 6 hours, 12 hours, 16 hours, and 24 hours), the mouse was sacrificed and around 30 to 40 mg of the tissues in abdominal fat and the liver were obtained. To 500 ul of a medium (RPMI, gibco) including 1 μM of cortisone (from Sigma Co. Ltd.) and 400 μM of NADPH (from Sigma Co. Ltd) was added the tissue as obtained (30-40 mg), which then reacted in a cell cultivator at 37° C. for 3 hours. After 50 ul of the reacted solution was taken and diluted with DMEM medium at a volume ratio of 1/10, the amount of cortisol being generated was measured by using a cortisol kit (assay designs Co. Ltd., ELISA kit) in accordance with the method set forth in the appended manual. From the results being measured, the degree of the inhibition was obtained by the conversion in comparison with the vehicle group (vehicle: 5% DMSO+5% cremophor in dw, the amount being proportionate to the body weight, i.e., the administration was made at the same volume as the drug being introduced).

Reference material: Published Aug. 15, 2005//JEM vol. 202 no. 4 517-527 The Rockefeller University Press % inhibition={(the amount of cortisol of the vehicle group–the amount of the cortisol of the group with the compound being administered)/(the amount of cortisol of the vehicle group)}×100

According to the above analyzing method, the efficacy of inhibiting 11b-HSD1 of the test compound in the target organ was calculated as % inhibition values, which are shown in Table 2 and Table 3.

TABLE 2

% inhibition values of 11b-HSD1 enzyme in the fat and the liver (10 mg/Kg, 2 hr)

| Compound | 11b-HSD1 % inhibition in the fat | 11b-HSD1 % inhibition in the liver |
|---|---|---|
| Example 1 | 91% | 85% |
| Example 2 | 84% | 68% |
| Example 18 | 58% | 62% |
| Example 19 | 51% | 50% |
| Example 64 | 51% | 61% |

TABLE 3

% inhibition values of 11b-HSD1 enzyme in the fat and the liver (20 mg/Kg, 6 hr)

| Compound | 11b-HSD1 % inhibition in the fat | 11b-HSD1 % inhibition in the liver |
|---|---|---|
| Example 1 | 83% | 70% |
| Example 2 | 85% | 44% |
| Example 18 | 65% | 61% |
| Example 26 | 71% | 47% |
| Example 27 | 80% | 65% |
| Example 30 | 72% | 69% |
| Example 34 | 96% | 92% |
| Example 38 | 98% | 98% |
| Example 39 | 98% | 96% |
| Example 40 | 63% | 38% |
| Example 43 | 70% | 59% |
| Example 64 | 57% | 48% |

What is claimed is:

1. A compound of Formula (I),

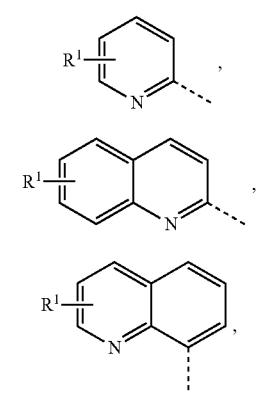

Formula (I)

a racemate thereof, or a pharmaceutically acceptable salt thereof, wherein
A is selected from the group consisting of Formulae (II) to (VIII):

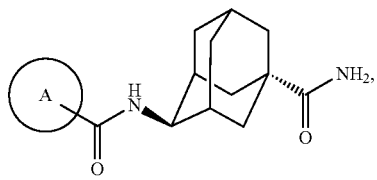
(II)

(III)

(IV)

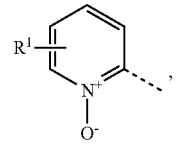
(V)

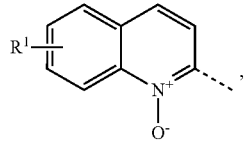
(VI)

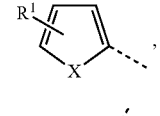
(VII)

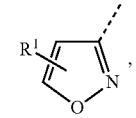
(VIII)

wherein X is O, S or N—Y;
Y is selected from the group consisting of —H, linear or branched $C_1$-$C_5$ alkyl and $C_3$-$C_5$ cycloalkyl;
$R^1$ is selected from the group consisting of —H, hydroxyl, linear or branched $C_1$-$C_5$ alkyl, $C_3$-$C_5$ cycloalkyl, —O—$R^3$, —N($R^4$)($R^5$), phenyl, pyridinyl, furanyl, thiazolyl, thiophenyl, hydro-1H-isoquinolinyl and isoxazolyl, wherein phenyl, pyridinyl, furanyl, thiazolyl, thiophenyl, hydro-1H-isoquinolinyl and isoxazolyl are substituted with one to three substituents independently selected from $R^2$;
$R^2$ is selected from the group consisting of —H, halo, linear or branched $C_1$-$C_5$ alkyl, $C_3$-$C_5$ cycloalkyl, trifluoromethyl, nitro, —O—$R^6$, and —N($R^7$)($R^8$);
$R^3$ is selected from the group consisting of —H, linear or branched $C_1$-$C_5$ alkyl, $C_3$-$C_5$ cycloalkyl, $C_5$-$C_6$ cycloalkylmethyl, $C_6$-$C_{10}$ arylmethyl, and $C_2$-$C_8$ heteroarylmethyl containing at least one of O, N and S;
$R^4$ and $R^5$ are each independently selected from the group consisting of —H and linear or branched $C_1$-$C_5$ alkyl, or $R^4$ and $R^5$ form 5- to 7-membered ring wherein the 5- to 7-membered ring is optionally substituted with phenyl;
$R^6$ is selected from the group consisting of —H and linear or branched $C_1$-$C_3$ alkyl; and
$R^7$ and $R^8$ are each independently selected from the group consisting of —H and linear or branched $C_1$-$C_3$ alkyl, or $R^7$ and $R^8$ form 5- to 7-membered ring.

2. The compound of claim 1, wherein $R^1$ is linear or branched $C_1$-$C_5$ alkyl, —O—$R^3$, phenyl substituted with one to three substituents independently selected from $R^2$ which is selected from the group consisting of —H, halo, linear or branched $C_1$-$C_5$ alkyl, trifluoromethyl, nitro and —O—$R^6$.

3. The compound of claim 1, wherein A is Formula (II):

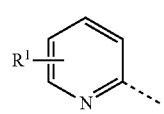
(II)

wherein:
R¹ is selected from the group consisting of —H, linear or branched $C_1$-$C_5$ alkyl, —O—R³, —N(R⁴)(R⁵) and 3,4-dihydro-1H-isoquinolinyl;
R³ is linear or branched $C_1$-$C_4$ alkyl, $C_6$-$C_{10}$ arylmethyl, or $C_2$-$C_8$ heteroarylmethyl containing at least one of O, N and S; and
R⁴ and R⁵ are independently selected from the group consisting of —H and linear or branched $C_1$-$C_5$ alkyl, or R⁴ and R⁵ form 5- to 7-membered ring wherein the 5- to 7-membered ring is optionally substituted with phenyl.

4. The compound of claim 1, wherein A is Formula (III):

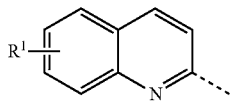

(III)

wherein:
R¹ is —H or —O—R³; and
R³ is linear or branched $C_1$-$C_4$ alkyl, $C_6$-$C_{10}$ arylmethyl or $C_5$-$C_6$ cycloalkylmethyl.

5. The compound of claim 1, wherein A is Formula (IV):

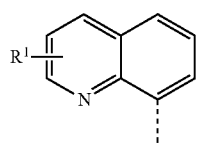

(IV)

wherein R¹ is —H or linear or branched $C_1$-$C_5$ alkyl.

6. The compound of claim 1, wherein A is Formula (V):

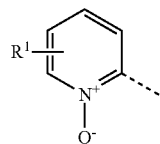

(V)

wherein:
R¹ is —H, linear or branched $C_1$-$C_5$ alkyl, or —N(R⁴)(R⁵); and
R⁴ and R⁵ are independently selected from the group consisting of —H and linear or branched $C_1$-$C_5$ alkyl.

7. The compound of claim 1, wherein A is Formula (VI):

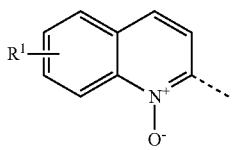

(VI)

wherein R¹ is —H or linear or branched $C_1$-$C_5$ alkyl.

8. The compound of claim 1, wherein A is Formula (VII):

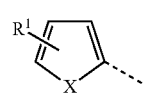

(VII)

wherein:
X is O, S, or N—Y;
Y is linear or branched $C_1$-$C_5$ alkyl;
R¹ is selected from the group consisting of —H, linear or branched $C_1$-$C_5$ alkyl, thiophenyl, and phenyl substituted with one to three substituents independently selected from R²; and
R² is —H, halo, linear or branched $C_1$-$C_5$ alkyl, nitro, or $C_1$-$C_3$ alkoxy.

9. The compound of claim 1, wherein A is Formula (VIII):

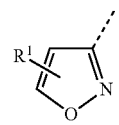

(VIII)

wherein:
R¹ is selected from the group consisting of —H, hydroxyl, linear or branched $C_1$-$C_5$ alkyl, phenyl, furanyl, thiophenyl and thiazolyl, wherein phenyl, furanyl, thiophenyl and thiazolyl are substituted with one to three substituents independently selected from R²; and
R² is —H, halo, linear or branched $C_1$-$C_5$ alkyl or $C_1$-$C_3$ alkoxy.

10. The compound of claim 1, which is selected from the group consisting of:
N-(5-carbamoyl-2-adamantyl)-5-phenylfuran-2-carboxamide,
N-(5-carbamoyl-2-adamantyl)-5-(4-chlorophenyl)furan-2-carboxamide,
N-(5-carbamoyl-2-adamantyl)-5-(4-nitrophenyl)furan-2-carboxamide,
N-(5-carbamoyl-2-adamantyl)-5-(4-methylphenyl)furan-2-carboxamide,
5-t-butyl-N-(5-carbamoyl-2-adamantyl)-1,2-oxazole-3-carboxamide,
N-(5-carbamoyl-2-adamantyl)-5-(3-methylphenyl)-1,2-oxazole-3-carboxamide,
N-(5-carbamoyl-2-adamantyl)-5-(2-methoxyphenyl)-1,2-oxazole-3-carboxamide,
N-(5-carbamoyl-2-adamantyl)-5-(2-methylphenyl)-1,2-oxazole-3-carboxamide,
N-(5-carbamoyl-2-adamantyl)-5-(3-methoxyphenyl)-1,2-oxazole-3-carboxamide,
N-(5-carbamoyl-2-adamantyl)-5-(furan-3-yl)-1,2-oxazole-3-carboxamide,
N-(5-carbamoyl-2-adamantyl)-5-(thiophen-3-yl)-1,2-oxazole-3-carboxamide,
N-(5-carbamoyl-2-adamantyl)-5-(3-fluorophenyl)-1,2-oxazole-3-carboxamide,
N-(5-carbamoyl-2-adamantyl)-5-(4-chlorophenyl)-1,2-oxazole-3-carboxamide,
N-(5-carbamoyl-2-adamantyl)-5-(2-methyl-1,3-thiazol-4-yl)-1,2-oxazole-3-carboxamide,
N-(5-carbamoyl-2-adamantyl)-6-methylpyridine-2-carboxamide, N-(5-carbamoyl-2-adamantyl)pyridine-2-carboxamide,
N-(5-carbamoyl-2-adamantyl)-1-methylpyrrole-2-carboxamide,
N-(5-carbamoyl-2-adamantyl)quinoline-2-carboxamide,
N-(5-carbamoyl-2-adamantyl)quinoline-8-carboxamide,
N-(5-carbamoyl-2-adamantyl)-8-hydroxyquinoline-2-carboxamide,
N-(5-carbamoyl-2-adamantyl)-5-thiophen-2-yl-thiophene-2-carboxamide,
N-(5-carbamoyl-2-adamantyl)thiophene-2-carboxamide,
N-(5-carbamoyl-2-adamantyl)-4-methylthiophene-2-carboxamide,
N-(5-carbamoyl-2-adamantyl)-5-methylthiophene-2-carboxamide,
N-(5-carbamoyl-2-adamantyl)-5-(4-fluorophenyl)furan-2-carboxamide,
N-(5-carbamoyl-2-adamantyl)-5-(3-chlorophenyl)furan-2-carboxamide,
N-(5-carbamoyl-2-adamantyl)-5-(2-chlorophenyl)furan-2-carboxamide,
N-(5-carbamoyl-2-adamantyl)-5-(4-methoxyphenyl)furan-2-carboxamide,
N-(5-carbamoyl-2-adamantyl)-5-(3,4-difluorophenyl)furan-2-carboxamide,
N-(5-carbamoyl-2-adamantyl)-5-(2-fluorophenyl)furan-2-carboxamide,
N-(5-carbamoyl-2-adamantyl)-5-(3,4-dichlorophenyl)furan-2-carboxamide,
N-(5-carbamoyl-2-adamantyl)-5-(3,5-dichlorophenyl)furan-2-carboxamide,
N-(5-carbamoyl-2-adamantyl)-5-(3-chlorophenyl)-1-methylpyrrole-2-carboxamide,
N-(5-carbamoyl-2-adamantyl)-1-methyl-5-phenylpyrrole-2-carboxamide,
N-(5-carbamoyl-2-adamantyl)-5-(4-chlorophenyl)-1-methylpyrrole-2-carboxamide,
N-(5-carbamoyl-2-adamantyl)-5-(4-fluorophenyl)-1-methylpyrrole-2-carboxamide,
N-(5-carbamoyl-2-adamantyl)-1-methyl-5-[4-(trifluoromethyl)phenyl]pyrrole-2-carboxamide,
N-(5-carbamoyl-2-adamantyl)-5-(2-chlorophenyl)-1-methylpyrrole-2-carboxamide,
N-(5-carbamoyl-2-adamantyl)-5-(2-fluorophenyl)-1-methylpyrrole-2-carboxamide,
N-(5-carbamoyl-2-adamantyl)-5-phenylthiophene-2-carboxamide,
N-(5-carbamoyl-2-adamantyl)-5-(4-chlorophenyl)thiophene-2-carboxamide,
N-(5-carbamoyl-2-adamantyl)-5-(3-chlorophenyl)thiophene-2-carboxamide,
N-(5-carbamoyl-2-adamantyl)-5-(2-chlorophenyl)thiophene-2-carboxamide,
N-(5-carbamoyl-2-adamantyl)-5-(2-fluorophenyl)thiophene-2-carboxamide,
N-(5-carbamoyl-2-adamantyl)-6-methoxypyridine-2-carboxamide,
N-(5-carbamoyl-2-adamantyl)-6-propoxypyridine-2-carboxamide,
N-(5-carbamoyl-2-adamantyl)-6-phenylmethoxypyridine-2-carboxamide,
N-(5-carbamoyl-2-adamantyl)-6-[(3,5-dimethyl-1,2-oxazol-4-yl)methoxy]pyridine-2-carboxamide,
N-(5-carbamoyl-2-adamantyl)-8-propoxyquinoline-2-carboxamide,
N-(5-carbamoyl-2-adamantyl)-8-methoxyquinoline-2-carboxamide,
N-(5-carbamoyl-2-adamantyl)-8-ethoxyquinoline-2-carboxamide,
N-(5-carbamoyl-2-adamantyl)-8-propan-2-yloxyquinoline-2-carboxamide,
N-(5-carbamoyl-2-adamantyl)-8-benzylmethoxyquinoline-2-carboxamide,
N-(5-carbamoyl-2-adamantyl)-8-(2-methylpropoxy)quinoline-2-carboxamide,
N-(5-carbamoyl-2-adamantyl)-8-(cyclohexylmethoxy)quinoline-2-carboxamide,
8-butane-2-yloxy-N-(5-carbamoyl-2-adamantyl)quinoline-2-carboxamide,
N-(5-carbamoyl-2-adamantyl)-6-(dimethylamino)pyridine-2-carboxamide,
N-(5-carbamoyl-2-adamantyl)-6-piperidin-1-ylpyridine-2-carboxamide,
N-(5-carbamoyl-2-adamantyl)-6-(diethylamino)pyridine-2-carboxamide,
N-(5-carbamoyl-2-adamantyl)-6-(propylamino)pyridine-2-carboxamide,
N-(5-carbamoyl-2-adamantyl)-6-(3,4-dihydro-1H-isoquinolin-2-yl)pyridine-2-carboxamide,
N-(5-carbamoyl-2-adamantyl)-6-(4-phenylpiperidin-1-yl)pyridine-2-carboxamide,
N-(5-carbamoyl-2-adamantyl)-6-methyl-1-oxidopyridin-1-ium-2-carboxamide,
N-(5-carbamoyl-2-adamantyl)-1-oxidoquinolin-1-ium-2-carboxamide, and
N-(5-carbamoyl-2-adamantyl)-6-(dimethylamino)-1-oxidopyridin-1-ium-2-carboxamide.

11. The compound of claim 3, which is selected from the group consisting of:
N-(5-carbamoyl-2-adamantyl)-6-methylpyridine-2-carboxamide,
N-(5-carbamoyl-2-adamantyl)pyridine-2-carboxamide,
N-(5-carbamoyl-2-adamantyl)-6-methoxypyridine-2-carboxamide,
N-(5-carbamoyl-2-adamantyl)-6-propoxypyridine-2-carboxamide,
N-(5-carbamoyl-2-adamantyl)-6-phenylmethoxypyridine-2-carboxamide,
N-(5-carbamoyl-2-adamantyl)-6-[(3,5-dimethyl-1,2-oxazol-4-yl)methoxy]pyridine-2-carboxamide,
N-(5-carbamoyl-2-adamantyl)-6-(dimethylamino)pyridine-2-carboxamide,
N-(5-carbamoyl-2-adamantyl)-6-piperidin-1-ylpyridine-2-carboxamide,
N-(5-carbamoyl-2-adamantyl)-6-(diethylamino)pyridine-2-carboxamide,
N-(5-carbamoyl-2-adamantyl)-6-(propylamino)pyridine-2-carboxamide,
N-(5-carbamoyl-2-adamantyl)-6-(3,4-dihydro-1H-isoquinolin-2-yl)pyridine-2-carboxamide, and
N-(5-carbamoyl-2-adamantyl)-6-(4-phenylpiperidin-1-yl)pyridine-2-carboxamide.

12. The compound of claim 4, which is selected from the group consisting of:
N-(5-carbamoyl-2-adamantyl)quinoline-2-carboxamide,
N-(5-carbamoyl-2-adamantyl)-8-hydroxyquinoline-2-carboxamide,
N-(5-carbamoyl-2-adamantyl)-8-propoxyquinoline-2-carboxamide,
N-(5-carbamoyl-2-adamantyl)-8-methoxyquinoline-2-carboxamide,
N-(5-carbamoyl-2-adamantyl)-8-ethoxyquinoline-2-carboxamide, N-(5-carbamoyl-2-adamantyl)-8-propan-2-yloxyquinoline-2-carboxamide,
N-(5-carbamoyl-2-adamantyl)-8-benzylmethoxyquinoline-2-carboxamide,
N-(5-carbamoyl-2-adamantyl)-8-(2-methylpropoxy)quinoline-2-carboxamide,
N-(5-carbamoyl-2-adamantyl)-8-(cyclohexylmethoxy)quinoline-2-carboxamide, and
8-butane-2-yloxy-N-(5-carbamoyl-2-adamantyl)quinoline-2-carboxamide.

13. The compound of claim 6, which is selected from the group consisting of:
N-(5-carbamoyl-2-adamantyl)-6-methyl-1-oxidopyridin-1-ium-2-carboxamide,
N-(5-carbamoyl-2-adamantyl)-1-oxidoquinolin-1-ium-2-carboxamide, and
N-(5-carbamoyl-2-adamantyl)-6-(dimethylamino)-1-oxidopyridin-1-ium-2-carboxamide.

14. The compound of claim 8, which is selected from the group consisting of:
N-(5-carbamoyl-2-adamantyl)-5-phenylfuran-2-carboxamide,
N-(5-carbamoyl-2-adamantyl)-5-(4-chlorophenyl)furan-2-carboxamide,
N-(5-carbamoyl-2-adamantyl)-5-(4-nitrophenyl)furan-2-carboxamide,
N-(5-carbamoyl-2-adamantyl)-5-(4-methylphenyl)furan-2-carboxamide,
N-(5-carbamoyl-2-adamantyl)-5-(4-fluorophenyl)furan-2-carboxamide,
N-(5-carbamoyl-2-adamantyl)-5-(3-chlorophenyl)furan-2-carboxamide,
N-(5-carbamoyl-2-adamantyl)-5-(2-chlorophenyl)furan-2-carboxamide,
N-(5-carbamoyl-2-adamantyl)-5-(4-methoxyphenyl)furan-2-carboxamide,
N-(5-carbamoyl-2-adamantyl)-5-(3,4-difluorophenyl)furan-2-carboxamide,
N-(5-carbamoyl-2-adamantyl)-5-(2-fluorophenyl)furan-2-carboxamide,
N-(5-carbamoyl-2-adamantyl)-5-(3,4-dichlorophenyl)furan-2-carboxamide,
N-(5-carbamoyl-2-adamantyl)-5-(3,5-dichlorophenyl)furan-2-carboxamide,
N-(5-carbamoyl-2-adamantyl)-1-methylpyrrole-2-carboxamide,
N-(5-carbamoyl-2-adamantyl)-5-(3-chlorophenyl)-1-methylpyrrole-2-carboxamide,
N-(5-carbamoyl-2-adamantyl)-1-methyl-5-phenylpyrrole-2-carboxamide,
N-(5-carbamoyl-2-adamantyl)-5-(4-chlorophenyl)-1-methylpyrrole-2-carboxamide,
N-(5-carbamoyl-2-adamantyl)-5-(4-fluorophenyl)-1-methylpyrrole-2-carboxamide,
N-(5-carbamoyl-2-adamantyl)-1-methyl-5-[4-(trifluoromethyl)phenyl]pyrrole-2-carboxamide,
N-(5-carbamoyl-2-adamantyl)-5-(2-chlorophenyl)-1-methylpyrrole-2-carboxamide,
N-(5-carbamoyl-2-adamantyl)-5-(2-fluorophenyl)-1-methylpyrrole-2-carboxamide,
N-(5-carbamoyl-2-adamantyl)-5-thiophen-2-ylthiophene-2-carboxamide,
N-(5-carbamoyl-2-adamantyl)thiophene-2-carboxamide,
N-(5-carbamoyl-2-adamantyl)-4-methylthiophene-2-carboxamide,
N-(5-carbamoyl-2-adamantyl)-5-methylthiophene-2-carboxamide,
N-(5-carbamoyl-2-adamantyl)-5-phenylthiophene-2-carboxamide,
N-(5-carbamoyl-2-adamantyl)-5-(4-chlorophenyl)thiophene-2-carboxamide,
N-(5-carbamoyl-2-adamantyl)-5-(3-chlorophenyl)thiophene-2-carboxamide,
N-(5-carbamoyl-2-adamantyl)-5-(2-chlorophenyl)thiophene-2-carboxamide, and
N-(5-carbamoyl-2-adamantyl)-5-(2-fluorophenyl)thiophene-2-carboxamide.

15. The compound of claim 9, which is selected from the group consisting of:
5-t-butyl-N-(5-carbamoyl-2-adamantyl)-1,2-oxazole-3-carboxamide,
N-(5-carbamoyl-2-adamantyl)-5-(3-methylphenyl)-1,2-oxazole-3-carboxamide,
N-(5-carbamoyl-2-adamantyl)-5-(2-methoxyphenyl)-1,2-oxazole-3-carboxamide,
N-(5-carbamoyl-2-adamantyl)-5-(2-methylphenyl)-1,2-oxazole-3-carboxamide,
N-(5-carbamoyl-2-adamantyl)-5-(3-methoxyphenyl)-1,2-oxazole-3-carboxamide,
N-(5-carbamoyl-2-adamantyl)-5-(furan-3-yl)-1,2-oxazole-3-carboxamide,
N-(5-carbamoyl-2-adamantyl)-5-(thiophen-3-yl)-1,2-oxazole-3-carboxamide,
N-(5-carbamoyl-2-adamantyl)-5-(3-fluorophenyl)-1,2-oxazole-3-carboxamide,
N-(5-carbamoyl-2-adamantyl)-5-(4-chlorophenyl)-1,2-oxazole-3-carboxamide, and
N-(5-carbamoyl-2-adamantyl)-5-(2-methyl-1,3-thiazol-4-yl)-1,2-oxazole-3-carboxamide.

16. The compound of claim 1, which is selected from the group consisting of:
N-(5-carbamoyl-2-adamantyl)-5-phenylfuran-2-carboxamide,
N-(5-carbamoyl-2-adamantyl)-5-(4-chlorophenyl)furan-2-carboxamide,
N-(5-carbamoyl-2-adamantyl)quinoline-2-carboxamide,
N-(5-carbamoyl-2-adamantyl)-5-(3-chlorophenyl)furan-2-carboxamide,
N-(5-carbamoyl-2-adamantyl)-5-(2-chlorophenyl)furan-2-carboxamide,
N-(5-carbamoyl-2-adamantyl)-5-(2-fluorophenyl)furan-2-carboxamide,
N-(5-carbamoyl-2-adamantyl)-1-methyl-5-phenylpyrrole-2-carboxamide,
N-(5-carbamoyl-2-adamantyl)-5-(2-chlorophenyl)-1-methylpyrrole-2-carboxamide,
N-(5-carbamoyl-2-adamantyl)-5-(2-fluorophenyl)-1-methylpyrrole-2-carboxamide,
N-(5-carbamoyl-2-adamantyl)-5-phenylthiophene-2-carboxamide,
N-(5-carbamoyl-2-adamantyl)-5-(2-chlorophenyl)thiophene-2-carboxamide, and
N-(5-carbamoyl-2-adamantyl)-1-oxidoquinolin-1-ium-2-carboxamide.

17. The compound of claim 1, which is selected from the group consisting of:
N-(5-carbamoyl-2-adamantyl)-5-phenylfuran-2-carboxamide,
N-(5-carbamoyl-2-adamantyl)-5-(4-chlorophenyl)furan-2-carboxamide,
N-(5-carbamoyl-2-adamantyl)quinoline-2-carboxamide,
N-(5-carbamoyl-2-adamantyl)quinoline-8-carboxamide, and N-(5-carbamoyl-2-adamantyl)-1-oxidoquinolin-1-ium-2-carboxamide.

18. A pharmaceutical composition comprising the compound, racemate or pharmaceutically acceptable salt thereof of claim 1 and a pharmaceutically acceptable adjuvant, diluent or carrier.

19. The pharmaceutical composition of claim 18, which is an oral composition.

20. A method for treating a disease caused by abnormal modulation of 11β-hydroxysteroid dehydrogenase type 1, comprising
  administering a therapeutically effective amount of the compound, racemate or pharmaceutically acceptable salt thereof of claim 1 to a patient in need thereof wherein the disease is diabetes, obesity, impaired glucose tolerance, hypertension or hyperlipidemia.

* * * * *